United States Patent
Schaff et al.

(10) Patent No.: US 10,197,480 B2
(45) Date of Patent: Feb. 5, 2019

(54) METHODS AND DEVICES FOR PROCESSING SAMPLES AND COUNTING CELLS

(71) Applicant: Sandstone Diagnostics, Inc., Livermore, CA (US)

(72) Inventors: Ulrich Schaff, Livermore, CA (US); Greg Sommer, Livermore, CA (US); Christopher Tomkins-Tinch, Rochester, NY (US)

(73) Assignee: SANDSTONE DIAGNOSTICS, INC., Livermore, CA (US)

( * ) Notice: Subject to any disclaimer, the term of this patent is extended or adjusted under 35 U.S.C. 154(b) by 163 days.

(21) Appl. No.: 14/441,158

(22) PCT Filed: Nov. 7, 2013

(86) PCT No.: PCT/US2013/068991
§ 371 (c)(1),
(2) Date: May 6, 2015

(87) PCT Pub. No.: WO2014/074737
PCT Pub. Date: May 15, 2014

(65) Prior Publication Data
US 2015/0300932 A1 Oct. 22, 2015
US 2016/0320276 A9 Nov. 3, 2016

Related U.S. Application Data

(60) Provisional application No. 61/723,665, filed on Nov. 7, 2012.

(51) Int. Cl.
*G01N 1/40* (2006.01)
*G01N 15/04* (2006.01)
(Continued)

(52) U.S. Cl.
CPC ......... *G01N 1/4077* (2013.01); *G01N 15/042* (2013.01); *G01N 15/06* (2013.01);
(Continued)

(58) Field of Classification Search
CPC ..... G01N 1/4077; G01N 15/042; G01N 15/06
(Continued)

(56) References Cited

U.S. PATENT DOCUMENTS 2,569,702 A 10/1951 Warner
3,401,696 A 9/1968 O'Brien
(Continued)

FOREIGN PATENT DOCUMENTS

AT 213017 T 2/2002
AU 8083891 A 12/1991
(Continued)

OTHER PUBLICATIONS https://trakfertility.com/ (Year: 2013).*
(Continued)

*Primary Examiner* — Jill A Warden
*Assistant Examiner* — Jacqueline Brazin
(74) *Attorney, Agent, or Firm* — Fenwick & West LLP

(57) ABSTRACT

A method and device performing the method for estimation of cell count, such as sperm cell count, is disclosed. The device may be a kit including a cartridge configured to hold fluid, such as seminal fluid, and an instrument configured to centrifuge the cartridge. The cartridge and instrument are configured such that, during operation or centrifugation, they are securely attached to each other. The cartridge has a component with a defined cross-sectional volume. The defined cross-sectional volume is used to mark the component with markings, allowing a user of the device to read the (Continued)

markings and estimate cell volume and, thus, concentration. Various embodiments of the device are disclosed.

65 Claims, 12 Drawing Sheets

(51) Int. Cl.
  *G01N 15/06* (2006.01)
  *G01N 15/00* (2006.01)
(52) U.S. Cl.
  CPC .............. *G01N 2001/4083* (2013.01); *G01N 2015/0065* (2013.01)
(58) Field of Classification Search
  USPC .......................................................... 422/72
  See application file for complete search history.

(56) References Cited

U.S. PATENT DOCUMENTS

| | | | |
|---|---|---|---|
| 3,518,164 A | 6/1970 | Andelin | |
| 4,125,375 A | 11/1978 | Hunter et al. | |
| 4,156,570 A | 5/1979 | Wardlaw | |
| 4,300,404 A | 11/1981 | Mehl et al. | |
| D267,118 S | 11/1982 | Bernett | |
| 4,530,816 A | 7/1985 | Douglas-Hamilton | |
| 4,683,579 A | 7/1987 | Wardlaw | |
| 4,799,599 A | 1/1989 | Herrmann | |
| 5,061,381 A * | 10/1991 | Burd .................. | G01N 21/07 210/198.1 |
| 5,068,089 A | 11/1991 | Ericsson et al. | |
| 5,122,284 A | 6/1992 | Braynin et al. | |
| 5,173,193 A | 12/1992 | Schembri | |
| 5,186,844 A | 2/1993 | Burd et al. | |
| 5,232,120 A | 8/1993 | Dunken et al. | |
| 5,242,606 A | 9/1993 | Braynin et al. | |
| 5,316,952 A | 5/1994 | Brimhall | |
| 5,342,790 A | 8/1994 | Levine et al. | |
| 5,358,690 A | 10/1994 | Guirguis | |
| 5,472,603 A | 12/1995 | Schembri | |
| 5,605,803 A | 2/1997 | Herr et al. | |
| 5,770,795 A | 6/1998 | Behar et al. | |
| 5,786,898 A | 7/1998 | Fitzpatrick | |
| D398,993 S | 9/1998 | Jones | |
| 5,807,360 A | 9/1998 | Shubin | |
| 5,895,749 A | 4/1999 | Alvarez | |
| 5,935,800 A | 8/1999 | Alvarez | |
| 6,153,148 A * | 11/2000 | Thomas ............... | B01L 3/50215 422/548 |
| 6,291,178 B1 | 9/2001 | Schneider | |
| 6,319,469 B1 | 11/2001 | Mian et al. | |
| 6,458,553 B1 | 10/2002 | Colin et al. | |
| 6,491,656 B1 | 12/2002 | Morris | |
| 6,632,399 B1 | 10/2003 | Kellogg et al. | |
| 6,864,046 B1 | 3/2005 | Prien | |
| 7,033,747 B2 | 4/2006 | Gordon et al. | |
| 7,077,000 B2 | 7/2006 | Gouldsworthy | |
| D529,170 S | 9/2006 | Wang | |
| 7,157,049 B2 | 1/2007 | Valencia et al. | |
| D560,813 S | 1/2008 | Matusuura | |
| 7,384,602 B2 | 6/2008 | Nagaoka et al. | |
| 7,758,810 B2 | 7/2010 | Lee et al. | |
| D631,558 S | 1/2011 | Harmston et al. | |
| 7,947,026 B2 | 5/2011 | Herr et al. | |
| D641,866 S | 7/2011 | Burgess et al. | |
| 7,993,315 B2 | 8/2011 | Matusuura | |
| 8,163,253 B1 | 4/2012 | Hartselle | |
| D660,451 S | 5/2012 | Matusuura | |
| 8,353,887 B2 | 1/2013 | Matusuura | |
| 8,475,422 B2 | 7/2013 | Wu | |
| 8,535,622 B2 | 9/2013 | Shany et al. | |
| 8,945,914 B1 | 2/2015 | Schaff et al. | |
| 8,962,346 B2 | 2/2015 | Schaff et al. | |
| D739,552 S | 9/2015 | Hoke | |
| 9,304,129 B2 | 4/2016 | Schaff et al. | |
| D762,299 S | 7/2016 | Matusuura | |
| 9,594,034 B1 | 3/2017 | Pompa | |
| 2002/0151040 A1 * | 10/2002 | O'Keefe et al. .... | B01F 13/0084 435/287.2 |
| 2002/0151043 A1 | 10/2002 | Gordon | |
| 2003/0127609 A1 * | 7/2003 | El-Hage ............... | G01N 21/253 250/574 |
| 2005/0011261 A1 | 1/2005 | Lyon | |
| 2005/0059163 A1 | 3/2005 | Dastane | |
| 2006/0068490 A1 * | 3/2006 | Tang ..................... | B01F 5/0603 435/287.2 |
| 2007/0031895 A1 | 2/2007 | Herr et al. | |
| 2007/0224591 A1 | 9/2007 | Gui et al. | |
| 2007/0286774 A1 * | 12/2007 | Barholm-Hansen ........................ | B01L 3/502746 422/400 |
| 2008/0202217 A1 | 8/2008 | Larsen | |
| 2009/0148869 A1 * | 6/2009 | Zaugg .................. | G01N 33/491 435/7.24 |
| 2009/0263848 A1 * | 10/2009 | Obermann ............ | G01N 33/58 435/29 |
| 2010/0240142 A1 | 9/2010 | Saiki et al. | |
| 2011/0084070 A1 | 4/2011 | Martheenal | |
| 2011/0086378 A1 | 4/2011 | Shany et al. | |
| 2011/0111981 A1 | 5/2011 | Love et al. | |
| 2011/0206646 A1 | 8/2011 | Alfonso et al. | |
| 2012/0052485 A1 * | 3/2012 | Shany .................. | A01N 1/0263 435/5 |
| 2012/0065047 A1 | 3/2012 | Chapman et al. | |
| 2012/0164751 A1 | 6/2012 | Liang et al. | |
| 2012/0234731 A1 | 9/2012 | Senftleber | |
| 2012/0282717 A1 | 11/2012 | Borch | |
| 2016/0023204 A1 | 1/2016 | Schaff et al. | |
| 2016/0047794 A1 | 2/2016 | Saiki | |
| 2016/0320276 A9 | 11/2016 | Schaff et al. | |
| 2017/0056878 A1 | 3/2017 | Peytavi et al. | |

FOREIGN PATENT DOCUMENTS

| | | |
|---|---|---|
| AU | 2925592 A | 6/1993 |
| AU | 5427699 A | 3/2000 |
| AU | 774508 B2 | 7/2004 |
| CA | 2346974 A1 | 12/1991 |
| CA | 2346975 A1 | 12/1991 |
| CA | 2347669 A1 | 12/1991 |
| CA | 2120244 A1 | 5/1993 |
| CA | 2343010 A1 | 3/2000 |
| CA | 2082827 C1 | 10/2001 |
| CN | 101802622 A | 8/2010 |
| CN | 103487596 A | 1/2014 |
| CN | 103499702 A | 1/2014 |
| DE | 69130986 T2 | 9/1999 |
| DE | 69900870 T2 | 11/2002 |
| EP | 0106536 | 4/1984 |
| EP | 0173811 A1 | 3/1986 |
| EP | 0532591 A1 | 3/1993 |
| EP | 0608006 A2 | 7/1994 |
| EP | 0611323 A1 | 8/1994 |
| EP | 0965388 * | 12/1999 |
| EP | 965388 A2 | 12/1999 |
| EP | 0965388 A2 | 12/1999 |
| EP | 1105457 A1 | 6/2001 |
| EP | 2072131 A1 | 6/2009 |
| EP | 2219034 A1 | 8/2010 |
| FR | 2782729 A1 | 3/2000 |
| GB | 2162312 A | 1/1986 |
| JP | S59-073766 A | 4/1984 |
| JP | H07-500910 A | 1/1995 |
| JP | 3256542 B2 | 2/2002 |
| JP | 2002-523083 A | 7/2002 |
| JP | 2006-505766 A | 2/2006 |
| JP | 2009-150733 A | 7/2009 |
| JP | 2009-150880 A | 7/2009 |
| JP | 2009-233532 A | 10/2009 |
| JP | 2009-300433 A | 12/2009 |
| JP | 2013-513794 A | 4/2013 |
| JP | 2013-541013 A | 11/2013 |

(56) References Cited

FOREIGN PATENT DOCUMENTS

| | | |
|---|---|---|
| JP | 5-508709 B2 | 6/2014 |
| JP | 2014-518374 A | 7/2014 |
| WO | WO 91/018656 A1 | 12/1991 |
| WO | WO 93/008893 A1 | 5/1993 |
| WO | WO 94/26299 | 11/1994 |
| WO | WO 2000/012674 A1 | 3/2000 |
| WO | WO 2009/060617 A1 | 5/2009 |
| WO | WO 2011/110469 A1 | 9/2011 |
| WO | WO 2011/137906 A1 | 11/2011 |
| WO | WO 2012/026970 A2 | 3/2012 |
| WO | WO 2012/055707 A1 | 5/2012 |
| WO | WO 2012/164552 A1 | 12/2012 |
| WO | WO 2014/191207 A1 | 12/2014 |
| WO | WO 2015/172255 A1 | 11/2015 |
| WO | WO 2016/188430 A1 | 12/2016 |

OTHER PUBLICATIONS https://trakfertility.com/products/trak-male-fertility-testing-system (Year: 2017).*

European Extended Search Report, European Application No. 13853032.4, dated Jun. 10, 2016, 9 pages.

Patent Cooperation Treaty, International Search Report and Written Opinion of the International Searching Authority, International Patent Application No. PCT/US2013/068991, dated Feb. 5, 2014, 13 Pages.

Abi-Samra, K. et al., "Infrared Controlled Waxes for Liquid Handling and Storage on a CD-Microfluidic Platform", The Royal Society of Chemistry; Lab Chip, 2010, pp. 723-726.

Arlington, S.A., "Alternative-site Diagnostic Testing," Analytical Proceedings, Apr. 1990, pp. 97-101, vol. 27.

Baldwin, R. L., "How Hofmeister Ion Interactions Affect Protein Stability," Biophysical Journal, Oct. 1996, pp. 2056-2063, vol. 71.

Boyko, M. et al., "Cell-Free DNA—A Marker to Predict Ischemic Brain Damage in a Rat Stroke Experimental Model", J Neurosurg Anesthesiol, Jul. 2011, pp. 222-228, vol. 23, No. 3.

Carney, J., "Rapid Diagnostic Tests Employing Latex Particles," Analytical Proceedings, Apr. 1990, pp. 99-100, vol. 27.

Curtis, R. A. et al., "A Molecular Approach to Bioseparations: Proteinprotein and Protein-Salt Interactions", Chemical Engineering Science, 2006, pp. 907-923, vol. 61.

Czeiger, D. et al., "Measurement of Circulating Cell-Free DNA Levels by a New Simple Fluorescent Test in Patients With Primary Colorectral Cancer," Am J Clin Pathol, 2011, pp. 264-270, vol. 135.

Glorikian, H. et al., "Smart-Consumables Product Development Strategy: Implications for Molecular Diagnostics", DX Directions, Spring 2010, pp. 12-16.

Goldshtein, H. et al., "A Rapid Direct Fluorescent Assay for Cell-Free DNA Quantification in Biological Fluids", Annals of Clinical Biochemistry, 2009, pp. 488-494, vol. 46.

Holmes, D. et al., "Leukocyte Analysis and Differentiation Using High Speed Microfluidic Single Cell Impedance Cytometry", Lab on a Chip, Oct. 21, 2009, pp. 2881-2889, vol. 9, No. 20.

Japanese Office Action, Japanese Application No. 2015-557080, dated Jan. 9, 2018, 18 pages.

Lee, B. S. et al., "A Fully Automated Immunoassay From Whole Blood on a Disc", Lab on a Chip, Mar. 5, 2009, pp. 1548-1555, vol. 9.

Lim, C. T. et al., "Bead-Based Microfluidic Immunoassays: The Next Generation," Biosensors and Bioelectronics, 2007, pp. 1197-1204, vol. 22.

Lo, Y. M. D. et al., "Plasma DNA Ax A Prognostic Marker in Trauma Patients," Clinical Chemistry, 2000, pp. 319-323, vol. 46, No. 3.

Madou, M. et al., "Lab on a CD", Annual Rev. Biomed. Eng., 2006, pp. 601-628, vol. 8.

Maes, M. L. et al., "Comparison of Sample Fixation and the Use of LDS-751 or Anti-CD45 for Leukocyte Identification in Mouse Whole Blood for Flow Cytometry," Journal of Immunological Methods, Jan. 30, 2007, pp. 79-86, vol. 319, No. 1-2.

Min, J. et al., "Functional Integration of DNA Purification and Concentration Into a Real Time Micro-PCR Chip", The Royal Society of Chemistry; Lab on a Chip, 2011, pp. 259-265, vol. 11.

Patent Cooperation Treaty, International Search Report and Written Opinion of the International Searching Authority, International Patent Application No. PCT/US2014/015170, May 23, 2014, 12 Pages.

Price, C. P. et al., "Light-Scattering Immunoassay", Principles and Practice of Immunoassay (Second Edition); Chapter 18, 1997, pp. 446-447.

Rhodes, A. et al., "Plasma DNA Concentration as a Predictor of Mortality and Sepsis in Critically Ill Patients," Critical Care, 2006, pp. 1-7, vol. 10, No. 2.

Rider, T. H. et al., "A B Cell-Based Sensor for Rapid Identification of Pathogens," www.sciencemag.org, Science, Jul. 11, 2003, pp. 213-215, vol. 301.

Riegger, L. et al., "Read-Out Concepts for Multiplexed Bead-Based Fluorescence Immunoassays on Centrifugal Microfluidic Platforms", Sensors and Actuators, 2006, pp. 455-462, vol. 126.

Schaff, U. Y. et al., "Whole Blood Immunoassay Based on Centrifugal Bead Sedimentation," Clinical Chemistry, 2011, pp. 753-761, vol. 57, No. 5.

Zhang, L. et al., "A New Biodosimetric Method: Branched DNA-Based Quantitative Detection of B1 DNA in Mouse Plasma," The British Journal of Radiology, Aug. 2010, pp. 694-701, vol. 83.

European Extended Search Report, European Application No. 14749441.3, dated Oct. 7, 2016, 10 pages.

Australian First Examination Report, Australian Application No. 2014214886, dated Apr. 7, 2017, 3 pages.

United States Office Action, U.S. Appl. No. 13/423,008.

Ziegler, A. et al., "Circulating DNA: A New Diagnostic Gold Mine?" Cancer Treatment Reviews, 2002, pp. 255-271, vol. 28.

Japanese Office Action, Japanese Application No. 2015-540917, dated Sep. 19, 2017, 4 pages (with concise explanation of relevance).

PCT International Search Report and Written Opinion, PCT Application No. PCT/US17/33710 ISR/WO, dated Aug. 24, 2017, 11 pages.

PCT International Search Report and Written Opinion, PCT Application No. PCT/US17/21571 ISR/WO, dated Jun. 5, 2017, 17 pages.

Japanese Office Action, Japanese Application No. 2015-540917, dated Apr. 24, 2018, 9 pages (with machine translation).

* cited by examiner

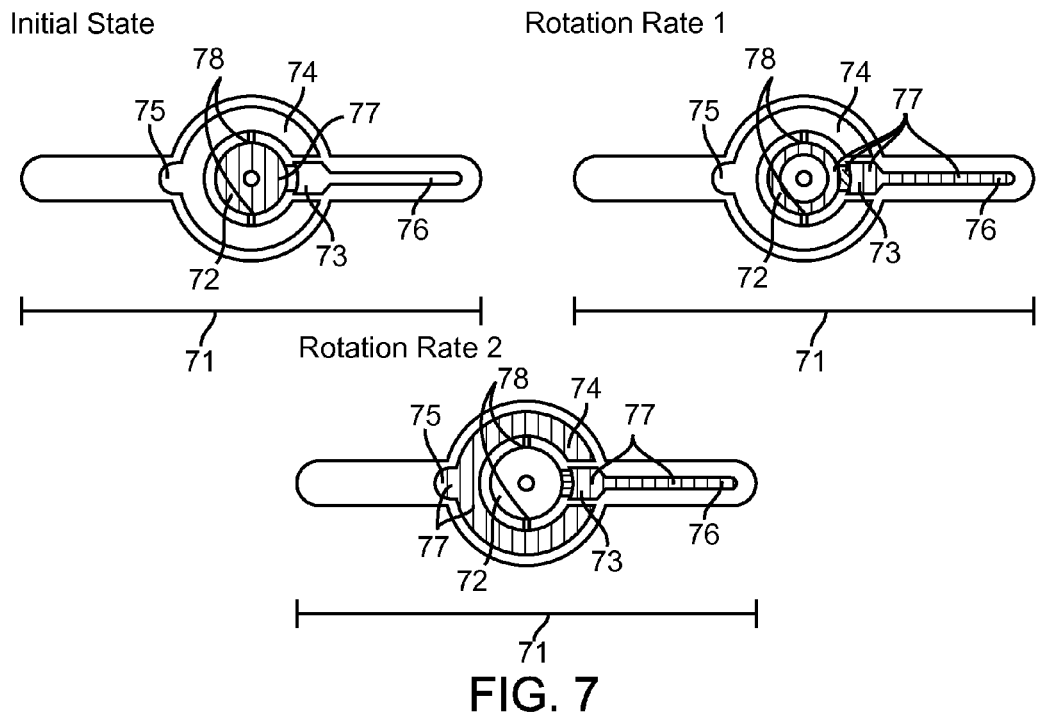
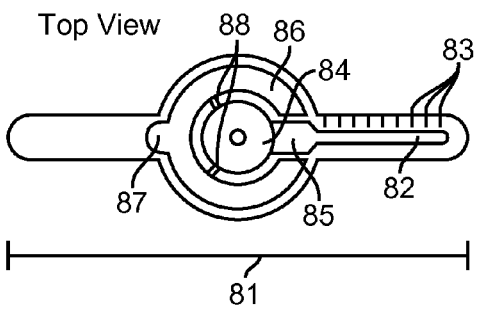
FIG. 8
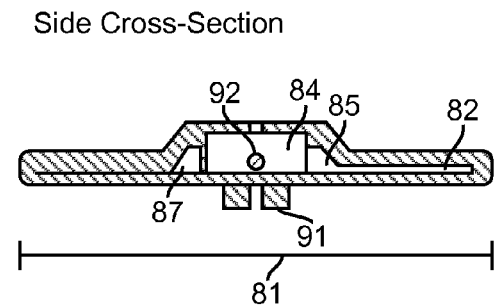
FIG. 9
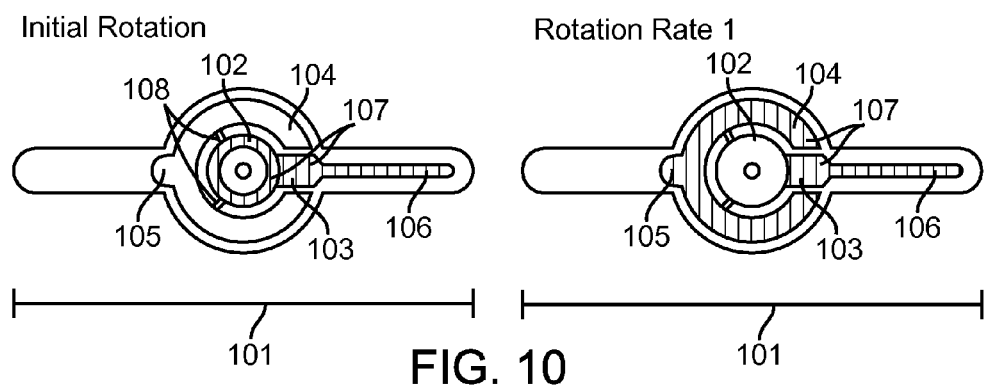
FIG. 10

Top View

Side Cross-Section

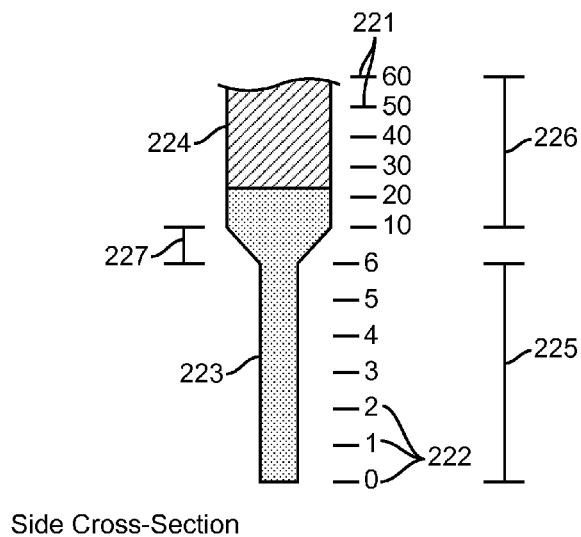
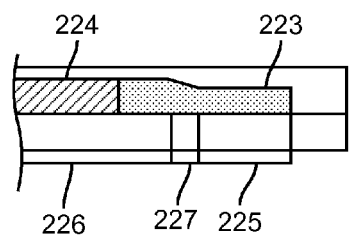
FIG. 22
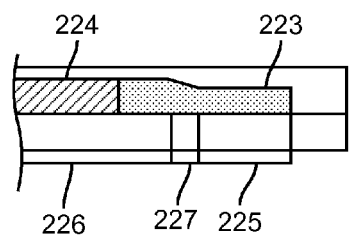
FIG. 23
FIG. 24
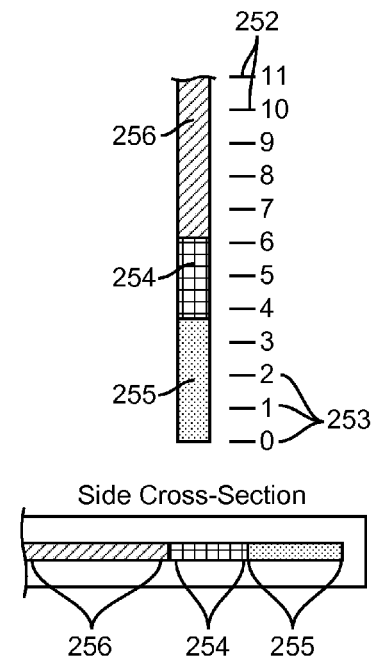
FIG. 25

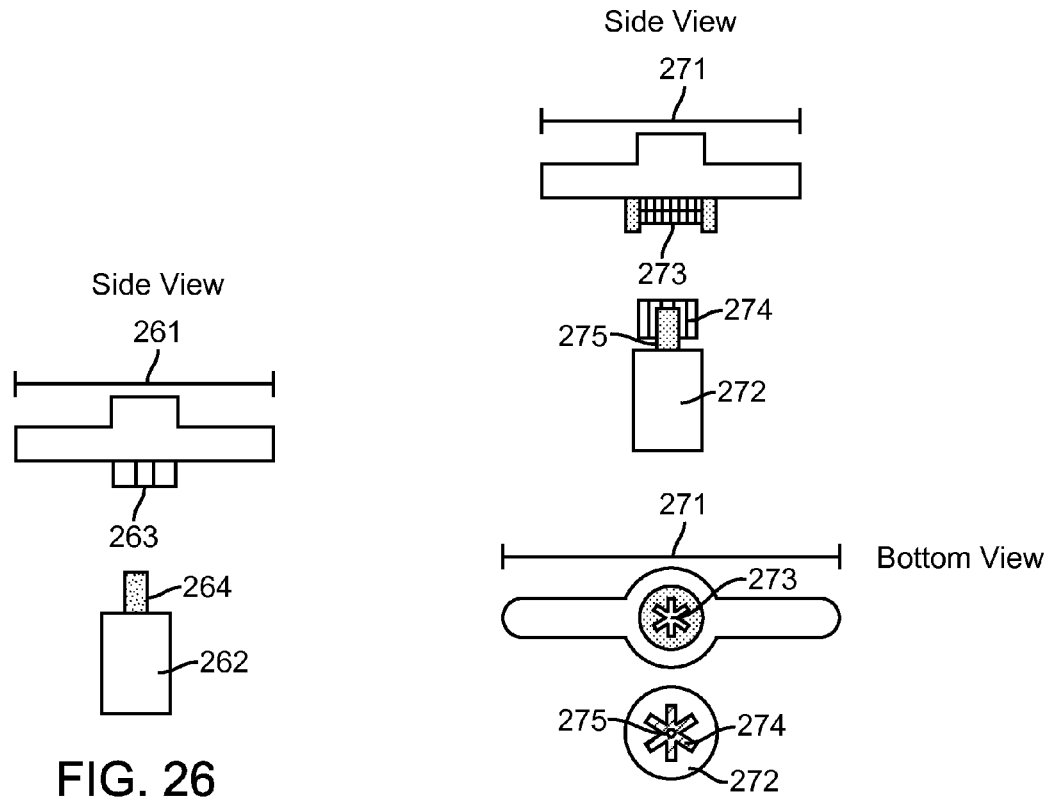
FIG. 26
FIG. 27
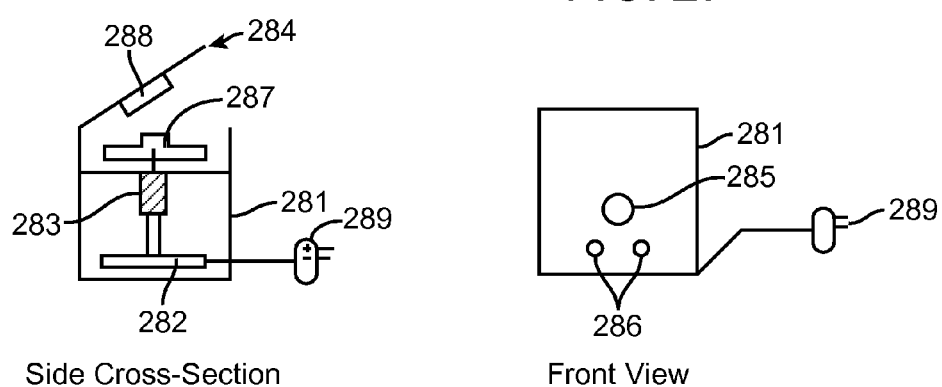
FIG. 28

METHODS AND DEVICES FOR PROCESSING SAMPLES AND COUNTING CELLS

CROSS REFERENCE TO RELATED APPLICATIONS

This application is a 35 U.S.C. 371 national stage filing of International Application No. PCT/US2013/068991, filed on Nov. 7, 2013, which claims the benefit of U.S. Provisional Application No. 61/723,665, filed Nov. 7, 2012, both of which are incorporated by reference in their entireties.

BACKGROUND

This invention relates generally to fluidic processing of biological samples for diagnostic purposes, sedimentation or centrifugal pelleting of suspended particulate matter, such as cells, separating particulate matter based on density, and enumerating particulates or cells by measurement of packed volume. More specifically, this invention relates to male fertility testing, and, in particular, sperm cell counting.

Worldwide, 10-20% of couples that attempt to conceive a new child have sub-optimal fertility. Difficulty in conceiving may be due to defects in either the male or the female reproduction system or a combination of the two, or due to other contributing factors. In approximately 40% of cases of infertility, the male partner is a contributing factor. The primary metrics available to evaluate male fertility are sperm count and motility. Sperm count is a concentration of sperm cells in semen and motility is a percentage of sperm cells capable of movement.

Conventional methods of evaluating male fertility comprise conducting clinical tests including microscopic examination to measure sperm count and motility. Semen samples for the clinical tests must be provided at the site of examination leading to privacy concerns for male subjects. Furthermore, providing a semen sample at the site of examination or in a clinical setting is widely perceived as awkward or embarrassing. This perception can deter male fertility testing for couples with difficulty conceiving despite the high prevalence of male fertility issues. A semen analysis test suitable for use in the home may be useful in cases where aversion to clinical conditions would otherwise deter testing. A few semen analysis test kits have been developed for use in the home, such as those in which a colored line is displayed when the concentration of sperm cells in a sample exceeds a particular number (e.g., 20 million per mL) or a color change is displayed when concentration of viable sperm cells in a sample exceeds a particular number (e.g., 10 million per mL). In these examples of test kits, the semen analysis tests provide a non-quantitative evaluation of sperm count. In cases where a low sperm count is correctable or sperm count varies over time, it may be desirable to have a quantitative estimate of the absolute sperm count and motility.

SUMMARY

The disclosed device and method is for estimation of particulate content in a biological sample, including estimation of cell, such as sperm cell, concentration by centrifugal sedimentation of cells in fluid, such as seminal fluid. The estimation is performed using an enclosed sedimentation column of defined cross-sectional area and by measuring height of a pellet of compacted cells within the sedimentation column with aid of a scale bar along the sedimentation column. In one embodiment, the device includes a cartridge containing the sedimentation column as well as channels and cavities for directing fluid and sedimenting particulates or cells. In other embodiments, the sedimentation column contains fluid of defined density to further separate cell populations by density. The sedimentation column may also include portions of variable cross-sectional area allowing for a visual of the height of sedimented cells in the sedimentation column to resemble measurements of cell concentration in the sedimented cells over a wider range of cell concentrations than otherwise possible. The device also includes or can be used with an instrument for rotating the cartridge at specified rotational rates for intervals of time.

Embodiments of the device can be used at home as home use test kits to estimate sperm cell concentration and motile sperm cell concentration, aiding in diagnosis and monitoring of male fertility disorders and allowing users to avoid having to provide samples in a clinical setting. When used in a fertility context, the device and method allow for a quantitative evaluation of sperm count and motility. The user can get a more accurate estimate of the actual sperm count rather than just determining whether the sperm count is above or below a certain threshold. The user can, for example, determine if sperm count and motility is only somewhat low, and so may be more readily correctable. Similarly, the user can determine if the sperm counts vary over time, possibly allowing the user to identify causative factors for sperm count, and otherwise track times when sperm counts are higher.

BRIEF DESCRIPTION OF THE FIGURES

FIG. 7 illustrates an initial state, rotation rate 1 state, and rotation rate 2 state of a cartridge during operation, in accordance with an embodiment of the invention.

FIG. 8 is a top view of a cartridge, in accordance with an embodiment of the invention.

FIG. 9 is a side cross-section view of a cartridge, in accordance with an embodiment of the invention.

FIG. 10 illustrates an initial rotation state and rotation rate 1 state of a cartridge during operation, in accordance with an embodiment of the invention.

FIG. 22 illustrates a top view and side cross-section view of a tapered sedimentation column, in accordance with an embodiment of the invention.

FIG. 23 illustrates a system for analyzing reflected light from fluid in a sedimentation column comprising a light source opposite of a detector, in accordance with an embodiment of the invention.

FIG. 24 illustrates a system for analyzing reflected light from fluid in a sedimentation column comprising a light source illuminating a transparent face of the cartridge, in accordance with an embodiment of the invention.

FIG. 25 illustrates a top view and side cross-section view of a sedimentation column with a density gradient, in accordance with an embodiment of the invention.

FIG. 26 illustrates a side view of a cartridge, an instrument, and a cavity-shaft configuration, in accordance with an embodiment of the invention.

FIG. 27 illustrates a side view and bottom view of a cartridge, an instrument, and a cavity-shaft configuration, in accordance with an embodiment of the invention.

FIG. 28 illustrates a side cross-section view and a front view of a cartridge and an instrument, in accordance with an embodiment of the invention.

Figure 1:
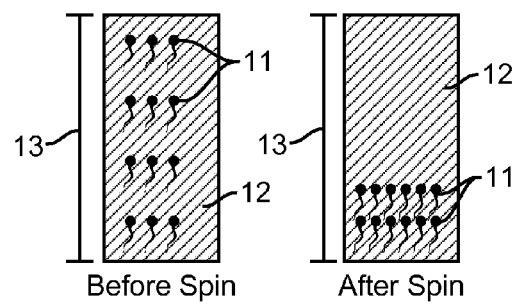
FIG. 1 is a representation of sedimentation before and after rotation, in accordance with an embodiment of the invention.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Various embodiments of estimation of sperm count and motility based on volume occupied by sperm cells packed into a column of defined cross-section following centrifugation is disclosed. The method is similar in principle to the hematocrit technique wherein concentration of red blood cells in a sample volume of blood is estimated by volume of packed red blood cells in a capillary following centrifugation. The hematocrit technique is a well-established technique for estimating red blood cell count in a blood sample based on packed volume of red blood cells following centrifugation from a known sample volume of blood. Estimation of cell count based on packed volume has also been applied to nucleated cell types such as leukocytes and leukocyte sub-types. For example, some hematology analyzers estimate red cell, granulocyte, and lymphocyte cell count from a sample volume of blood centrifuged in a capillary. In many cases, a scalebar incorporated in the hematocrit capillary provides a visual reference and aids in estimation of cell concentration. Thus, packed volume sedimentation provides an easy-to-read method for estimating cell concentration, which can be applied to counting sperm cells.

However, previous implementations used for blood analysis are wholly impractical for direct application to semen analysis. For humans, the average concentration of red blood cells in blood is approximately 100 times higher than the average sperm concentration in semen. Also, the considerably higher viscosity of semen prevents uptake of a defined volume of sample by capillary action as is necessary for operation of hematocrit tubes and retards or prevents sedimentation of sperm cells upon centrifugation. Semen is also highly heterogeneous in composition (i.e. initially contains regions of high and low sperm concentration) unlike blood, and therefore requires homogenization to achieve reproducible measurements of concentration. For these reasons, different fluidic structures and modified sample processing steps are necessary to form a sedimented pellet of sperm cells that can be measured. Furthermore, the previously described hematocrit and blood analysis techniques require heavy and expensive centrifuges or dedicated analyzers to spin and contain the sedimentation capillaries, making them impractical for the general public. Nonetheless, if a means of mitigating the considerable challenges listed above was developed, packed volume sedimentation could provide a simple-to-use means of estimating sperm count.

In one embodiment, the estimation of cell count is provided for through use of a device that can be included in a kit. The device comprises a cartridge including a packed volume column and a motorized instrument for spinning the cartridge. The cartridge may attach to the motorized instrument, for example, using a frictional press fit between a motor shaft of the motorized instrument and the cartridge, or using a plurality of magnets. In addition, the device, when prepared as a kit, may also comprise a fluid transfer device and a sample collection cup to assist with transferring the sample to the cartridge. The cartridge may be a disposable cartridge, and a user can use a new cartridge for each sample.

Throughout this description, the disclosed method and device is presented in terms of a method and device for manipulating semen samples for fertility analysis. However, these examples are provided for the purpose of illustration only. The method and device can also be used with other suitable fluids or samples for this method comprising packed volume sedimentation. For instance, the device may also be applied to examining packed volume of particulates in motor oil or to automated quantification of red blood cells or leukocytes in a sample volume of blood. Other types of particulates or solids in other types of samples can also be quantified or otherwise analyzed with the devices and methods described throughout. In some embodiments, the samples are food, soil or other materials, and in other embodiments, the samples are biological samples, such as blood, stool, semen, and other samples that might come from an organism, such as a human.

An embodiment of the device for estimating concentration of cells 11 based on volume occupied by cells 11 in a packed volume is illustrated in FIG. 1. The cells 11 are initially suspended in a fluid 12. In one embodiment, the cells 11 are sperm cells and the fluid 12 is seminal fluid. Following rotation, the cells 11 are packed at the bottom of a sedimentation chamber 13 and the sedimented cells occupy a volume proportional to a number of cells 11 initially suspended in the fluid 12.

Figure 2:
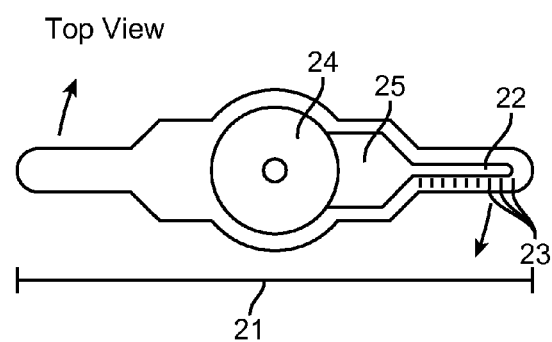
FIG. 2 is a top view of a cartridge, in accordance with an embodiment of the invention.
Figure 3:
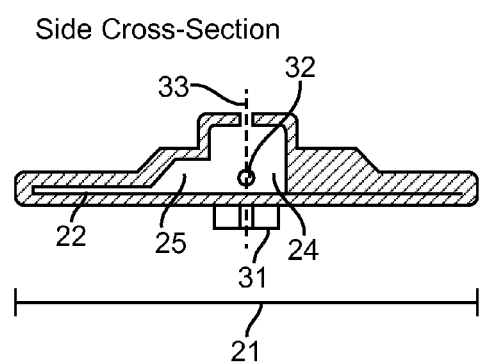
FIG. 3 is a side cross-section view of a cartridge, in accordance with an embodiment of the invention.

A top view and a side cross-section view of an embodiment of a cartridge 21 are illustrated in FIGS. 2 and 3, respectively. A top view of the cartridge 21 is shown in FIG. 2 and a cross-sectional side view in FIG. 3. The cartridge 21 can be constructed from a variety of materials including a polymer or other similar material. All cartridges described throughout the detailed description may be constructed in the same manner. In general, features or materials described for any cartridge included herein can be included or used in any of the other cartridges described herein, as well. Cartridges described herein can be the cartridge 21 or embodiments of the cartridge as described per figure.

The cartridge 21 may comprise a sedimentation column 22 that comprises metering marks 23. The metering marks 23 aid a user in determining volume of sedimented cells. The cartridge may also comprise a central sample entry cavity 24 and a sample directing cavity 25 with a defined volume, the sample directing cavity 25 in fluid communication with the central sample entry cavity 24. In other words, the fluid is capable of moving between the central sample entry cavity 24 and the sample directing cavity 25. For example, when a volume of fluid equal to the volume of the sample directing cavity 25 is added to the central sample entry cavity 24 and the cartridge 21 is rotated clockwise or counterclockwise about a central axis 33 of the cartridge 21, the fluid collects in the sample directing cavity 25. With further rotation, for example at 2000-10000 RPM for 2-10 minutes, cells from the fluid are packed at the bottom of the sedimentation column 22 and the sedimented cells can be read by the user using the metering marks 23. The cartridge 21 may additionally include a hub attachment 31 configured to securely connect the cartridge 21 to a motorized instrument for spinning the cartridge 21. In one embodiment, the cartridge 21 may connect or attach to the motorized instrument for spinning the cartridge 21 using a plurality of magnets. For all cartridge and instrument descriptions herein, a plurality of magnets can be used to attach the cartridge and the instrument.

In addition, the cartridge 21 may hold a reagent pellet 32 or be coated with chemical reagents, such as digestive enzymes, to provide fluorescent cell labels, contrast dyes, specific density beads, or, in the embodiment of sperm cells, reduce semen viscosity to facilitate easier reading by the user. These reagents may be freeze dried.

Figure 4:
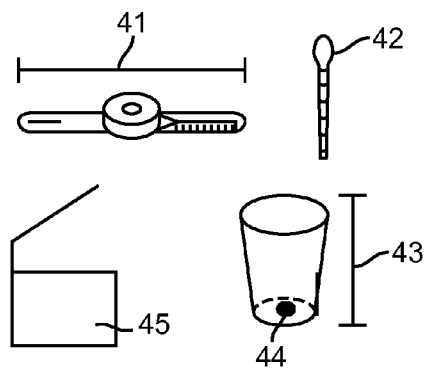
FIG. 4 illustrates a device as a kit, in accordance with an embodiment of the invention.

An embodiment of the device as a kit is shown in FIG. 4. The device comprises items used for counting cells including a cartridge 41 such as a disposable cartridge, a fluid transfer device 42 such as a bulb pipette, other type of pipette, or a syringe, a collection cup 43 for collecting fluid, and an instrument 45 configured to rotate the cartridge 41. The user transfers a defined sample volume into the cartridge 41 using the transfer device 42. The transfer device 42 may have a level mark configured to assist in measuring the defined sample volume. For the cartridge designs embodied in FIGS. 5-13, a non-precise amount of sample may be transferred to the cartridge by the user. The collection cup 43 may comprise a reagent pellet 44 or be coated with chemical reagents, such as those described above regarding reagent pellet 32, and the reagents or pellets may be freeze dried. Similarly, for all collection cups comprising a reagent pellet herein, the collection cup may comprise the reagent pellet or may be coated with chemical reagents, such as those described above regarding regent pellet 32, and the reagents and/or pellets may be freeze dried. To rotate or spin the cartridge 41, the user can attach the cartridge 41 to the instrument 45. In one embodiment, the cartridge 41 and instrument 45 comprise additional components to securely attach the cartridge 41 to the instrument 45.

Figure 5:
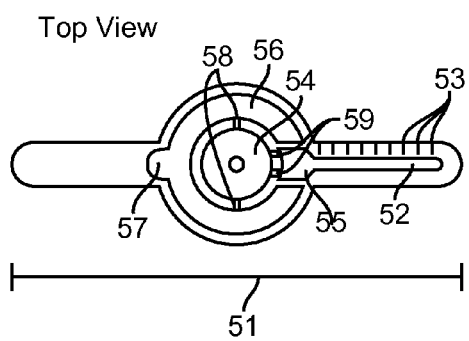
FIG. 5 is a top view of a cartridge, in accordance with an embodiment of the invention.
Figure 6:
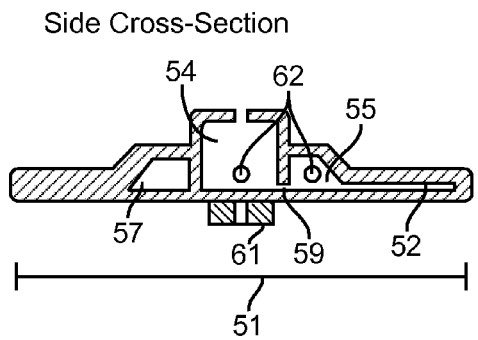
FIG. 6 is a side cross-section view of a cartridge, in accordance with an embodiment of the invention.

A top view and a side cross-section view of an embodiment of a cartridge 51 are illustrated in FIGS. 5 and 6, respectively. The cartridge 51 may comprise a sedimentation column 52 that contains metering marks 53. The metering marks 53 are configured to aid the user in determining volume of sedimented cells. The cartridge 51 may also comprise a central sample entry cavity 54 and a sample directing cavity 55 with a defined volume. The cartridge 51 may also comprise an overflow chamber 56 with a counterbalance cavity 57 intended to counterbalance the sample directing cavity 55. The overflow chamber 56 is connected to the central sample entry cavity 54 by shallow channels 58. The shallow channels 58 allow the sample in the cartridge 51 to move from the central sample entry cavity 54 to the overflow chamber 56 during rotation, for example during a second round of rotation, as further described in FIG. 7. The sample directing cavity 55 is connected to the central sample entry cavity 54 by additional shallow channels 59. The additional shallow channels 59 in one embodiment include a larger depth or diameter than the depth or diameter, respectively, of the shallow channels 58. The shallow channels 59 allow the sample to move from the central sample entry cavity 54 to the sample directing cavity 55, for example during a first round of rotation, further described in FIG. 7. The shallow channels 58 and additional shallow channels 59 have a depth or diameter configured such that fluid wetting and surface tension forces prevent movement of the sample through the channels 58 and 59 unless a threshold rotation rate is exceeded by the cartridge 51, for example, during centrifugation. The threshold rotation rate necessary for causing movement of the sample through shallow channels 59 is based at least in part on diameter or depth of the shallow channels. For example, the threshold rotation rate will increase as diameter or depth of shallow channels decrease. The cartridge 51 may additionally include a hub attachment 61 configured to securely connect the cartridge 51 to a motorized instrument for spinning the cartridge 51 during, for example, centrifugation. The cartridge 51 may hold a reagent pellet 62 or be coated with chemical reagents, as described above regarding the reagent pellet 32.

An initial state, first rotation rate state and second rotation rate state of an embodiment of fluid movement within a cartridge 71 are described in FIG. 7, respectively. Fluid 77 is initially loaded into a central sample entry cavity 72. In the initial state, the shaded portion of the cartridge 72 represents the fluid 77. Upon rotation at a first rotation rate, for example in a range of 100-4000 RPM, preferably in a range of 500-2000 RPM, the fluid enters a sample directing cavity 73 with a defined volume during a first time period until the sample directing cavity 73 is full as seen in the rotation rate 1 state. The overflow chamber 74 may comprise a counterbalance cavity 75. The cartridge 71 comprises a sedimentation column 76.

As seen in the rotation rate 1 state, since the cross-sectional area of shallow connecting channels 78 is smaller than the cross-sectional area of an overflow chamber 74, the fluid 77 is prevented from entering the overflow chamber 74 during the first rotation rate. Balance of fluid surface tension and wetting forces overcoming effective gravitational force prevents entry of the fluid 77 into the overflow chamber 74. In addition, the counterbalance cavity 75 assists in counterbalancing the sample directing cavity 73, which fluid 77 can also enter during the first rotation rate. Upon rotation of the cartridge 71 at a second rotation rate (e.g. 2000-10000 RPM, 2-10 minutes) during a second time period, the fluid remaining in the central sample entry cavity 72 enters the overflow chamber 74 and counterbalance cavity 75, as shown in the rotation rate 2 state. With centrifugation for the second time period at the second rotation rate, cells in the sample directing cavity 73 become compacted in the sedimentation column 76. Then, the pellet of sedimented and compacted cells can be read by the user with a cell pellet height proportional to amount of cells initially contained in the sample directing cavity 73 and sedimentation column 76 during rotation rate 1 state. Due to excess fluid being directed to the overflow channels 74 during the second time period, cells can be measured from a precise amount of fluid. In some embodiments, additional rotations can be performed for additional time periods. This can be true for any embodiments described herein. In further embodiments, only a single rotation is performed for an interval of time, and, in some cases, this single rotation provides compacting of the cells. This can be true for any embodiments described herein.

A top view and a side cross-section view of another embodiment of a cartridge 81 are illustrated in FIGS. 8 and 9, respectively. The cartridge 81 may comprise a sedimentation column 82 that contains metering marks 83. The metering marks 83 are configured to aid the user in determining volume of sedimented cells. The cartridge 81 may also comprise a central sample entry cavity 84 and a sample directing cavity 85 with a defined volume. The cartridge 81 may also comprise an overflow chamber 86 with a counterbalance cavity 87 intended to counterbalance the sample directing cavity 85. The overflow chamber 86 is connected to the central sample entry cavity 84 by shallow connecting channels 88. Unlike the sample directing cavity 85 being connected to the central sample entry cavity 84 by shallow channels such as the shallow channels 59 in FIG. 5, the sample directing cavity 85 can be in direct fluid communication with the central sample entry cavity 84. The sample directing cavity 85 and the central sample entry cavity 84 are connected in a manner similar to that illustrated in FIGS. 2 and 3. The cartridge 81 may also comprise a hub attachment 91 configured to securely connect the cartridge 81 to a motorized instrument for spinning during centrifugation. The cartridge 81 may comprise a reagent pellet 92 or be coated with chemical reagents, as described above regarding the reagent pellet 32.

An initial rotation state and a first rotation rate state of an embodiment of the fluid movement within a cartridge 101 are described in FIG. 10. Fluid 107 is initially loaded into a central sample entry cavity 102, as shown in the initial state. The cartridge is intended to be rotated at a first rotation rate (e.g. 2000-10000 RPM) for a time interval (e.g. 2-10 minutes) and distribute fluid in one step, allowing a simplified instrument design. Upon rotation at the single rate, fluid enters a sample directing cavity 103 and a sedimentation column 106, the sample directing cavity 103 and the sedimentation column 106 comprising a defined volume and being in direct fluid communication with the central sample entry cavity 102, unlike in FIGS. 5 and 7 where the sample directing cavity and central sample entry cavity are connected by channels. As the rotation rate of the cartridge 101 accelerates and reaches the first rotation rate, a rate necessary to overcome surface tension and wetting forces in shallow channels 108 connecting the central sample entry cavity 102 and an overflow chamber 104 is exceeded, and the fluid remaining in the central sample entry cavity 102 will enter the overflow chamber 104 and a counterbalance cavity 105, as illustrated in the rightmost illustration of FIG. 10. Therefore the fluid remaining in the sample directing cavity 103 is the only fluid that contributes to the volume of sedimented cells in the sedimentation column 106 following centrifugation. With continued centrifugation (e.g., 2-10 minutes), cells within the sample directing cavity 103 become compacted in the sedimentation column 106 where a sedimented cell pellet can be read by the user with a pellet height proportional to amount of cells initially contained in the fluid inside the sample directing cavity 103 and sedimentation column 106 during the rotation 1 state.

Figure 11:
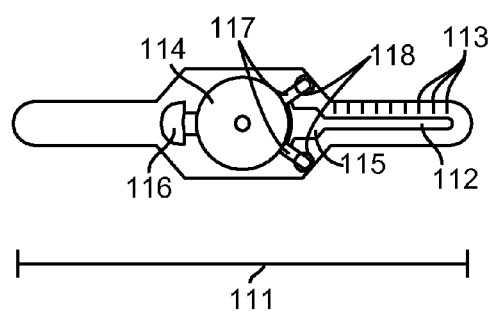
FIG. 11 illustrates a top view of a cartridge, in accordance with an embodiment of the invention.
Figure 12:
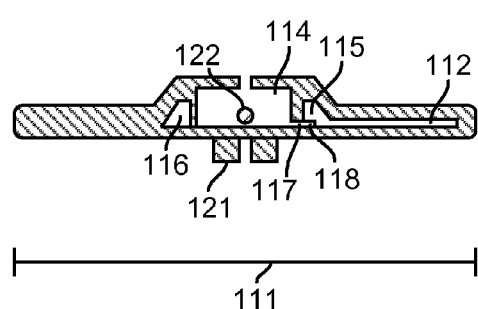
FIG. 12 illustrates a side cross-section view of a cartridge, in accordance with an embodiment of the invention.

A top view and a side cross-section view of another embodiment of a cartridge 111 are illustrated in FIGS. 11 and 12, respectively. The cartridge 111 may comprise a sedimentation column 112 that comprises metering marks 113. The metering marks 113 are configured to aid the user in determining volume of sedimented cells. The cartridge 111 may also comprise a central sample entry cavity 114 and a sample directing cavity 115. The cartridge 111 may also comprise a counterbalance cavity 116 for counterbalancing the sample directing cavity 115. The sample directing cavity 115 is connected to the central sample entry cavity 114 by angled shallow channels 117, wherein the angled shallow channels 117 comprise an extension 118 for retaining or storing sedimented cells. For example, the angled shallow channels 117 are angled radially outward from the center of the cartridge 111 with respect to the sedimentation column 112. While the sedimentation column 112 is located radially outward from the center of the cartridge 111 along a first radial axis, the angled shallow channels 117 are also located radially outward from the center of the cartridge 111 along a second radial axis and a third radial axis, where the second radial axis and the third radial axis are not the first radial axis. The cartridge 111 may additionally include a hub attachment 121 configured to securely connect the cartridge 111 to a motorized instrument for spinning the cartridge 111 during, for example, centrifugation. The cartridge 111 may comprise one or more reagent pellets 122 or be coated with chemical reagents, as described above regarding the reagent pellet 32.

Figure 13:
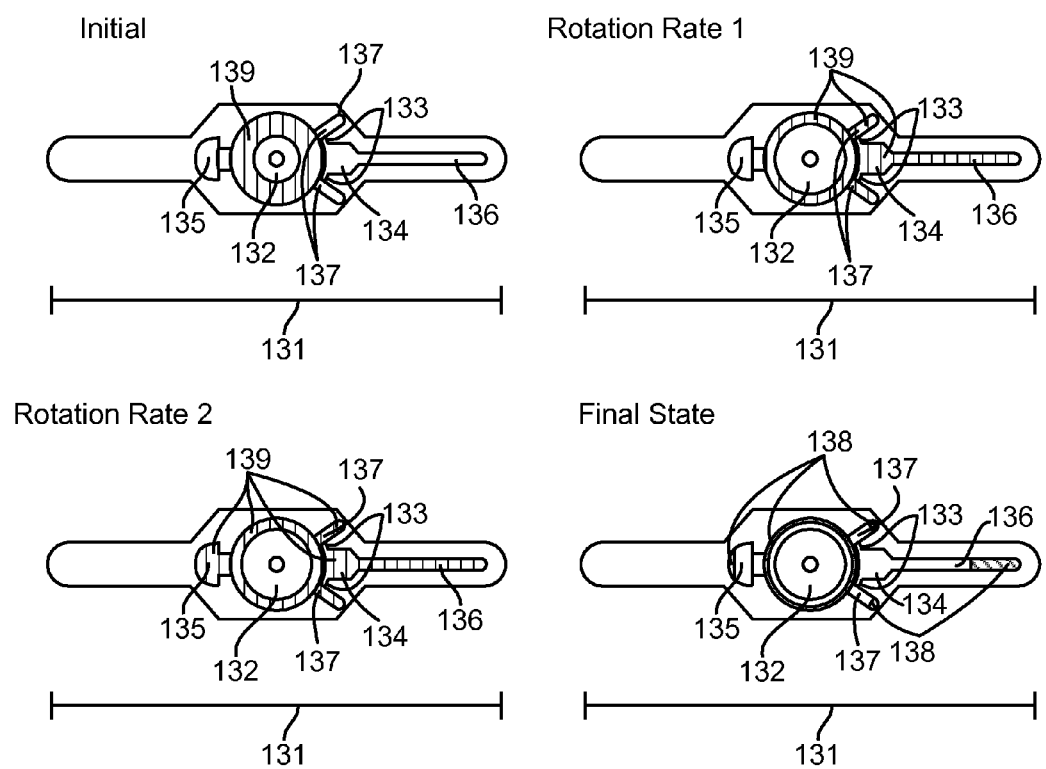
FIG. 13 illustrates an initial state, rotation rate 1 state, rotation rate 2 state, and final state of a cartridge during operation, in accordance with an embodiment of the invention.

An initial state, first rotation state, second rotation state, and final state of an embodiment of a fluid movement within a cartridge 131 are described in FIG. 13. Fluid 139 is loaded into a central sample entry cavity 132, as seen in the initial state. Upon rotation, fluid travels from central sample entry cavity 132 into channel extensions 137, connecting channels 133, and into a sample directing cavity 134 with a defined volume. The first rotation rate state is shown in the rotation rate 1 state. When rotation rate of the cartridge exceeds a rate necessary to overcome surface tension, the fluid remaining in the central sample entry cavity 132 enters an optional counterbalance chamber 135. The second rotation rate state is shown in the rotation rate 2 state. With further rotation of the cartridge 131, for example at 2000-10000 RPM for 2-10 minutes, cells within the directing cavity 134 become compacted in a sedimentation column 136 where the sedimented pellet can be read by the user with a pellet height proportional to amount of cells contained in the sample directing cavity 134 and sedimentation column 136 during the rotation rate 1 state. The final state is shown in the final state. Cells initially contained in channel extensions 137 and central sample entry cavity during rotation rate 1 state are trapped in channel extensions 137 and therefore do not contribute to volume of sedimented cells in the sedimentation column 136. Locations where compacted cells will collect in the shown cartridge design of FIG. 13 are marked as 138. An advantage of the design of the cartridge 131 is that less material and less complexity is required for manufacturing the cartridge 131 than previously described cartridge designs due to lack of overflow chambers. Measurement of volume of cells from only a volume of interest of fluid can be achieved by capturing sedimented cells from excess fluid in an alternate location from the sedimentation column 136 rather than physically removing excess fluid from the central sample entry cavity.

Figure 14:
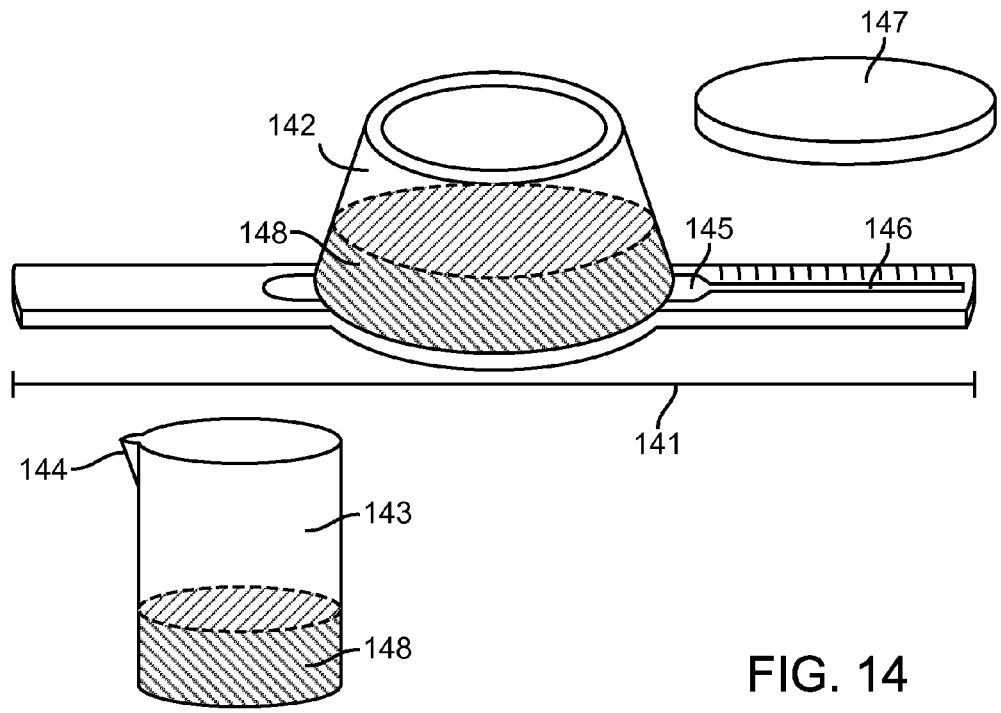
FIG. 14 illustrates a device as a kit, in accordance with an embodiment of the invention.

FIG. 14 demonstrates a kit for cell, sperm cell or other particle measurement including a cartridge 141, the cartridge 141 an alternative embodiment of the cartridge described in FIGS. 11 and 12 (though cartridges of the other Figures can be used too). The sample inlet cavity 142 is increased in size to accommodate a fluid 148 in its entirety. In one embodiment, the fluid is seminal fluid and the cavity comprises a volume that exceeds a maximum fluid volume produced by a human male, where the maximum fluid volume is about 5 milliliters. This design is configured to directly collect a fluid for analysis by the central cavity 142. Optionally, the fluid may be collected in a collection cup 143. The collection cup 143 may comprise a spout 144 for pouring the fluid into the sample inlet cavity 142 of the cartridge 141. Upon centrifugation, such as at 2000-10000 RPM for 2-10 minutes, cells within a sample directing cavity 145 become compacted in a sedimentation column 146 while cells in the fluid remaining in the sample inlet cavity 142 are retained therein. Either the sample inlet cavity 142 or the collection cup 143 may contain chemical reagents for enzymatic digestion, contrast enhancement, or other assay enhancing functions. A lid 147 that is configured to attach to the cartridge 141 during centrifugation to prevent fluid spillage may be included in the kit. The design of FIGS. 5 and 6 or the design of FIGS. 8 and 9 may comprise sufficiently large overflow cavities, allowing for analysis of a greater volume of fluid, such as up to 5 milliliters.

Figure 15:
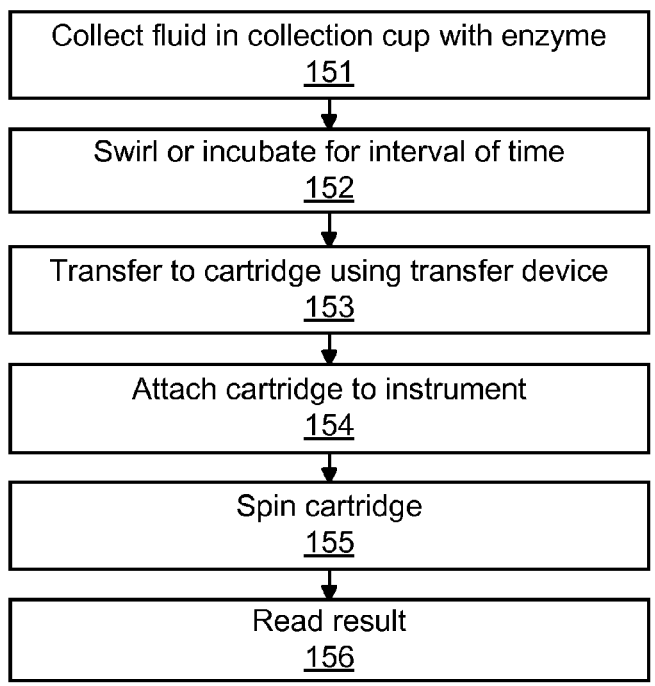
FIG. 15 is a flowchart of a method for preparing fluid for an estimation of cell count, in accordance with an embodiment of the invention.

FIG. 15 is a flowchart of an embodiment of a method for estimating sperm count based on volume occupied by sperm cells packed into a column of defined cross-section following centrifugation. Different embodiments may perform the steps in the method in a different order, omit certain steps, and/or perform additional steps. In one embodiment, the method is performed using a kit comprising a collection cup, a cartridge, a transfer device and an instrument. Any cartridge or instrument design described herein may be used in the method.

The user collects 151 a sample or fluid in the collection cup. In one embodiment, the collection cup comprises digestive enzymes such as chymotrypsin, trypsin, bromelain, or papain for accelerating liquefaction of the fluid. The fluid is swirled or agitated 152, for example by the user, in the collection cup (or the sample can be otherwise agitated, such as agitated by the instrument once it is placed in the instrument). Swirling or agitating the fluid accelerates dissolution of the enzyme into the fluid. An interval of time (e.g., of 1-30 minutes) elapses to allow the enzyme to liquefy the fluid. A portion of the fluid is then transferred 153 to the cartridge using a transfer device, such as a syringe or bulb transfer pipette. In one embodiment, the cartridge is capped with a lid or sticker following input of the fluid. The cartridge is attached 154 to the instrument, wherein the instrument comprises a motor configured to rotate the cartridge. Optionally, the instrument may accelerate the cartridge in one direction and then an opposite direction for an interval of time, mechanically agitating the fluid, encouraging homogenization and reduced viscosity for more consistent measurements. The instrument may also accelerate the cartridge in one direction, allow it to come to a stop, then repeat for an interval of time to provide mechanical agitation. The instrument spins 155 or rotates the cartridge at a rotation rate (e.g., for 2-10 minutes at 2000-10000 RPM). Optionally, the cartridge is spun at a reduced rotation rate for an interval of time (e.g., for 1-5 minutes) to allow for controlled expansion of compacted cells in a sedimentation column of the cartridge. After rotation, the cartridge is halted by the instrument and the user reads 156 the result by estimating cell count or concentration in the fluid based on height of compacted cell pellet in the sedimentation column of the cartridge. In some embodiments, the instrument comprises a digital reading the user can read (e.g., digital reading on a user interface of the instrument). All embodiments of the instrument described herein may comprise a digital reading on a user interface of the instrument. In one embodiment, the instrument comprises a lid, wherein the lid comprises one or more magnets and the instrument comprises one or more sensors configured to detect magnetic fields. The one or more magnets and one or more sensors are placed within the lid and the instrument such that, when the lid is closed on the instrument, the one or more magnets in the lid and the one or more sensors in the instrument are a distance away, where the distance is less than a threshold distance necessary for the one or more sensors to detect a magnetic field of the one or more magnets in the lid and thus detect that the lid is closed on the instrument. In another embodiment, the one or more magnets can be in the instrument and the one or more sensors in the lid of the instrument. The magnet and sensor configuration described here can be applied to any instrument described herein.

Figure 16:
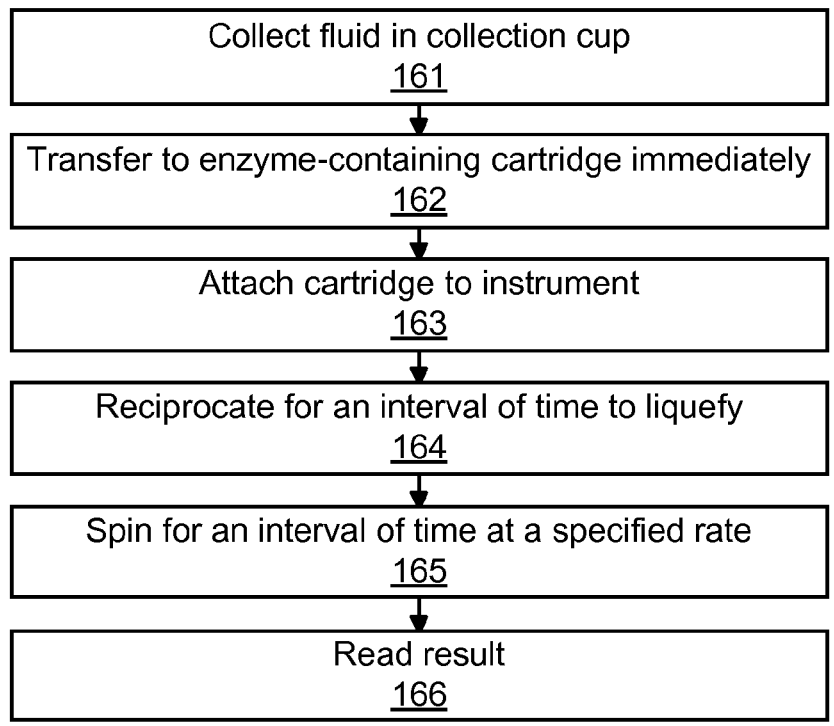
FIG. 16 is a flowchart of a method for preparing fluid for an estimation of cell count with enzymes, in accordance with an embodiment of the invention.

FIG. 16 is a flowchart of an embodiment of a method for estimating sperm concentration based on volume occupied by sperm cells packed into a column of defined cross-section following centrifugation. Different embodiments may perform the steps in the method in a different order, omit certain steps, and/or perform additional steps. In one embodiment, the method is performed using a kit comprising a collection cup, a cartridge, a transfer device and an instrument. Any cartridge or instrument design described herein may be used in the method.

The fluid or sample is collected 161 by a user in the collection cup. The user may swirl or agitate the fluid to aid in homogenization. A portion of the fluid is then transferred 162 to the cartridge using the transfer device immediately or before coagulation of the fluid. The transfer device may be a syringe or bulb transfer pipette. The cartridge may optionally comprise a lid or sticker configured to securely cap the cartridge following input of the fluid in the cartridge. The cartridge is attached 163 to the instrument. The instrument comprises a motor and the motor is configured to rotate, spin, or reciprocate 164 the cartridge for an interval of time to liquefy the fluid. The instrument may alternately accelerate the cartridge in one direction and then the other for an interval of time to mechanically agitate the fluid, encouraging homogenization and reduced viscosity of the fluid for more consistent measurements. Enzymes enclosed in the cartridge can act on the agitated fluid (e.g., for 1-30 minutes) to promote liquefaction of the fluid. The cartridge is spun 165 by the instrument for an interval of time at a specified rate (e.g., for 2-10 minutes at 2000-10000 RPM). Optionally, the cartridge may then be spun 165 at a reduced RPM (e.g., for 1-5 minutes) to allow for controlled expansion of compacted cells in the sedimentation column. After this spin is done, the cartridge is halted by the instrument and the user may read 166 a result of an estimate of the cell concentration in the fluid from the height of a compacted cell pellet in the sedimentation column.

Figure 17:
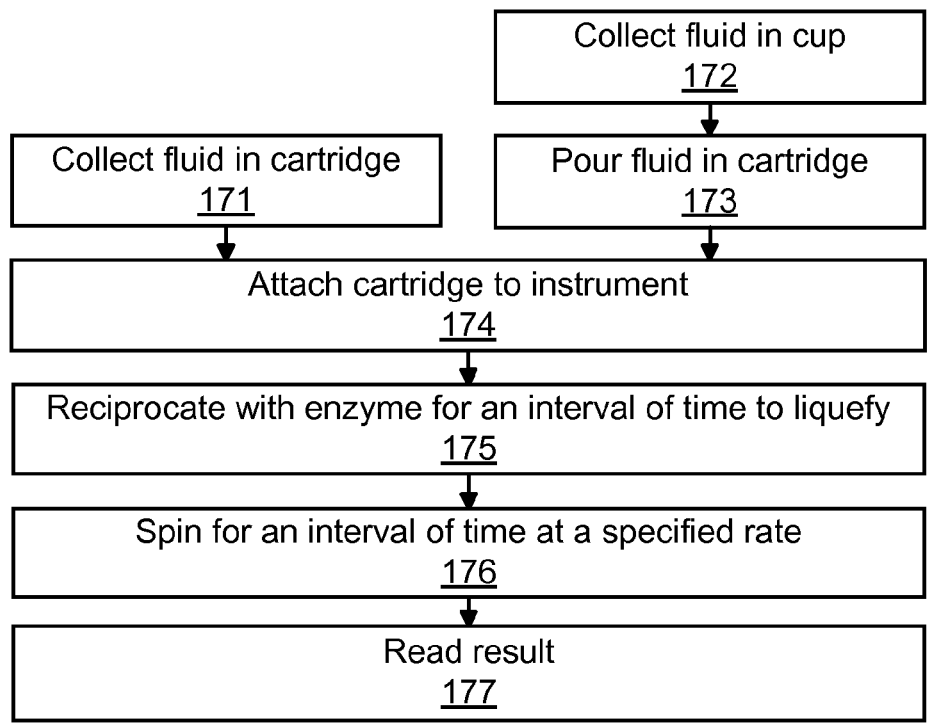
FIG. 17 is a flowchart of a method for preparing fluid for an estimation of cell count, in accordance with an embodiment of the invention.

FIG. 17 is a flowchart of an embodiment of a method for estimating sperm concentration based on volume occupied by sperm cells packed into a column of defined cross-section following centrifugation. Different embodiments may perform the steps in the method in a different order, omit certain steps, and/or perform additional steps. In one embodiment, the method is performed using a kit comprising a collection cup, a cartridge, and an instrument. Any cartridge or instrument design described herein may be used in the method.

The fluid or sample is collected 171 in the cartridge or collected 172 in the collection cup. In the case the sample is collected 172 in the collection cup, the entire fluid is poured 173 into the cartridge. The cartridge may optionally comprise a lid configured to securely cap the cartridge following input of the fluid in the cartridge. The cartridge is attached 174 to the instrument. The instrument comprises a motor and the motor is configured to rotate, spin or reciprocate 175 the cartridge. The instrument may alternately accelerate the cartridge in one direction and then the other for an interval of time to mechanically agitate the fluid, encouraging homogenization and reduced viscosity of the fluid for more consistent measurements. Enzymes enclosed in the cartridge can act on the agitated fluid (e.g., for 1-30 minutes) to promote liquefaction of the fluid. The cartridge is spun 176 for an interval of time at a specified rate (e.g., for 2-10 minutes at 2000-10000 RPM). Optionally, the cartridge may then be spun 176 at a reduced RPM (e.g., 100-2000 RPM for 1-5 minutes) to allow for controlled expansion of compacted cells in the sedimentation column. After this spin is done, the cartridge is halted by the instrument and the user may read 177 a result of an estimate of the cell concentration in the fluid from the height of compacted cells in the sedimentation column.

For each of the methods described in FIGS. 15-17, the user may perform all of the steps himself at home using a cartridge and/or kit as described throughout this description and using an instrument for rotating the cartridge, such as those described herein. In other embodiments, the user provides the sample in the cartridge, but then the cartridge is delivered to a clinic, such as a fertility center, that performs the rotation/centrifugation of the sample using an instrument at the clinic, such as those described herein. In this case, the user performs the collection 151, 161, 172, 171 steps and possibly other steps, such as the swirl/incubate 152, transfer 153, 162, and pour 173 steps, but the clinic may perform the attachment 154, 163, 174 of the cartridge to the instrument along with the steps that follow. In another embodiment, the user provides the sample in a holding device and it is transferred to the cartridge at the clinic. In this case, the clinic performs the transfers and pour and possibly the swirl/incubate steps. Thus, the method can include just the subset of steps performed by the user or the subset of steps performed by the clinic.

FIGS. 18-25 describe various embodiments of configurations of the sedimentation column. Any of the described various embodiments may be incorporated into the cartridge designs described in FIGS. 3-14.

Figure 18:
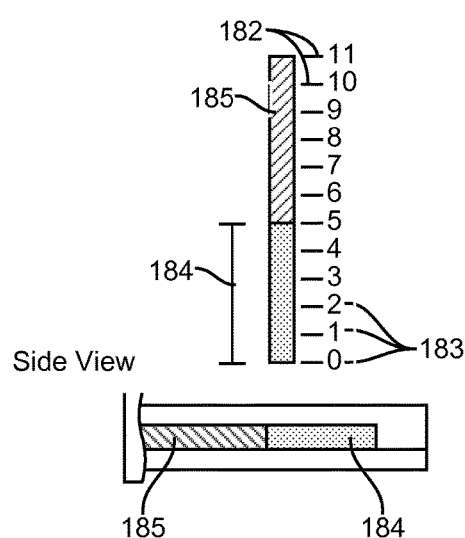
FIG. 18 illustrates a top view and a side view of a sedimentation column, in accordance with an embodiment of the invention.

FIG. 18 shows an enlargement of a top view and a side view of a sedimentation column, the sedimentation column comprising metering marks 182 and numbers 183. After cells are compacted by centrifugation, the height of a resulting pellet 184 may be determined visually by differences in reflectance between cells in the pellet 184 and fluid 185 or by other means including fluorescent cell labels. The user can estimate initial concentration of cells in the fluid by reading the number 183 closest to a metering mark 182 closest to the interface between the cells 184 and the fluid 185.

Figure 19:
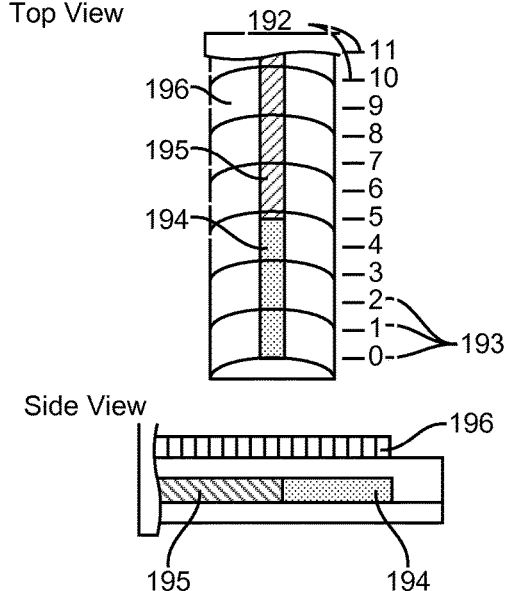
FIG. 19 illustrates a top view and a side view of a sedimentation column with a lens, in accordance with an embodiment of the invention.

FIG. 19 shows an enlargement of a top view and a side view of a sedimentation column, the sedimentation column comprising metering marks 192 and numbers 193. The sedimentation column comprises a lens 196 configured to magnify the sedimentation column and size of the sedimentation column. The lens 196 can be integrated into the sedimentation column during fabrication, for example, by injection molding of polymer. The presence of the lens 196 may allow the user to visualize an interface between a pellet 194 and fluid 195 more easily. In one embodiment, the lens 196 is cylindrical in shape. Other types and shapes of lenses can also be used. After cells are compacted by centrifugation, the height of the pellet 194 may be determined visually by differences in reflectance between the cells and fluid 195 or by other means including fluorescent cell labels. The user can estimate the initial concentration of cells in the fluid by reading the number 193 closest to a metering mark 192 closest to the interface between the cells 194 and the fluid 195.

Figure 20:
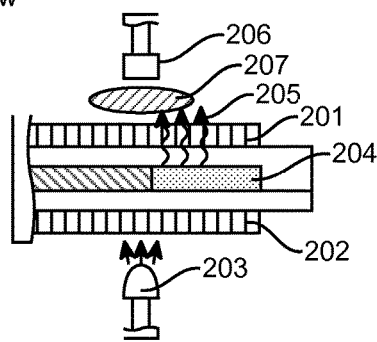
FIG. 20 illustrates a system for analyzing reflected light of fluid in a sedimentation column with lenses along the sedimentation column, in accordance with an embodiment of the invention.

FIG. 20 shows a side view of an alternate embodiment of a sedimentation column intended for use with fluorescent analysis. A top lens 201 and a bottom lens 202 are integrated into a top surface and a bottom surface of the sedimentation column, respectively. In one embodiment, the lenses are cylindrical in shape. Other types and shapes of lenses can also be used. A fluorescent excitation light source 203, such as an LED, filtered lamp, or laser, emits light such that it is focused on the sedimentation column by the bottom lens 202. Labeled cells in a pellet 204 are excited by the impinging light and emit a light 205 of a wavelength longer than a threshold wavelength. The light 205 is focused by the top lens 201 onto a detector 206. The detector 206 may be a CCD camera, photodiode, photomultiplier, or human eye. A selective filter 207 may be placed between the detector 206 and the sedimentation column to selectively pass the wavelengths of the light 205 emitted by the excited cells.

The detector 206 may determine the height of the pellet 204 by scanning along the sedimentation column and can be based on total fluorescent signal.

Figure 21:
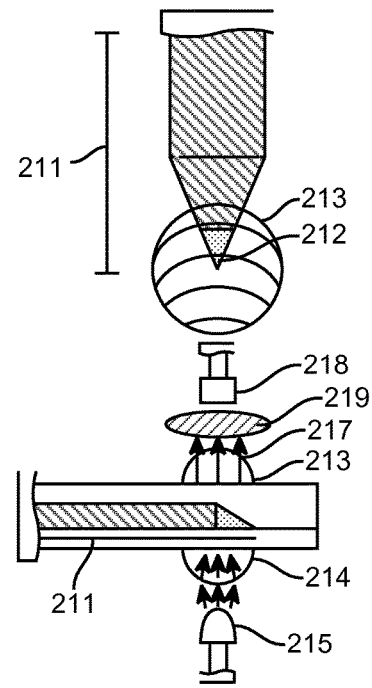
FIG. 21 illustrates a system for analyzing reflected light of fluid in a sedimentation column with lenses on the end of the sedimentation column, in accordance with an embodiment of the invention.

FIG. 21 shows an alternate embodiment of a sedimentation column 211 intended for use with fluorescent analysis. Geometry of the sedimentation column 211 causes cells to be compacted into a pellet 212 with small surface area following centrifugation. A top lens 213 and a bottom lens 214 are integrated into a top surface and a bottom surface of the sedimentation column, respectively. The top lens 213 and the bottom lens 214 may be spherical or aspheric lenses. A fluorescent excitation light source 215, such as an LED, filtered lamp, or laser emits light such that the light is focused on the pellet 212 by the bottom lens 214. Cells in the pellet 212 may be labeled with fluorescent dyes, such as acrinidine orange which are active only within nucleic acid containing cells. Labeled cells in the pellet 212 are excited by the impinging light and emit light 217 of a wavelength longer than a threshold wavelength. The light 217 is focused by the top lens 213 onto a detector 218 which may be a CCD camera, CMOS sensor, photodiode, photomultiplier, or human eye. A selective filter 219 may be placed between the detector 218 and the sedimentation column 211 to selectively pass the light 217 emitted by the excited cells 217. The detector 218 may determine a total number of cells present based on total integrated fluorescence emitted by the cells in the pellet 212.

FIG. 22 shows an alternate embodiment of a sedimentation column intended for use in estimating a wide range of cell concentrations. The sedimentation column comprises metering marks 221 and numbers 222. After cells are compacted by centrifugation, height of a resulting pellet 223 may be determined visually by differences in light scattering and reflectance between the cells in the pellet 223 and fluid 224 or by other means including fluorescent cell labels. The user can estimate initial concentration of cells in the fluid by reading the number 222 closest to a metering mark 221 closest to an interface between the cells in the pellet 223 and the fluid 224. In this embodiment, the sedimentation column is tapered comprising a section of a high cross-sectional area 225 exceeding a reference cross-sectional area and a low cross-sectional area 226 not exceeding a reference cross-sectional area with a transition area 227 in between the sections 225 and 226. In this embodiment, a pellet comprising low cell concentration will be accommodated by a portion comprising low cross-sectional area 226, while a pellet comprising substantially higher cell concentrations will be accommodated by a portion comprising high cross-sectional area 225. The metering marks 221 and numbers 222 are adjusted for the different cross-sectional areas, allowing a user to accurately estimate cell concentration. To one skilled in the art, it is apparent that many variations of sedimentation column taper are possible. For instance more than one transition area 227 may be integrated into the sedimentation column to create multiple sections with varying cross-sectional area. For example, the multiple sections may comprise sections with sequentially increasing or decreasing cross-sectional areas. In another example, cross-sectional area may continuously increase or decrease along the sedimentation column to accommodate a wide range of cell concentrations and metering marks 221 and numbers 222 can be adjusted accordingly. The multiple sections may also comprise varying cross-sectional areas such that a visual of the height of the pellet 223 in the sedimentation column corresponds to cell concentration of the pellet 223. For example, if a user sees a pellet 223 with a height of 4 mm, there are 4 metering marks 221, each metering mark equidistant from each other along the pellet 223. In addition, there may be the numbers 222 per metering mark. In an embodiment where the visual of the height does not correspond to cell concentration of the pellet 223, there may be 4 metering marks 221 not equidistant from each other along the pellet 223.

FIG. 23 shows an embodiment of a sedimentation column 231 enclosed by an upper layer 232 of polymer and a lower layer 233 of polymer. The upper layer 232 and lower layer 233 may be joined by processes including ultrasonic welding, laser welding, or thermal bonding. A fluorescent excitation light source 234, such as an LED, filtered lamp, or laser, emits light such that the light impinges a pellet 235 in the sedimentation column 231. The lower layer 233 may be dyed with filtering agents configured to selectively pass light emitted by the light source 234 to enhance contrast. Cells in the pellet 235 may be labeled with fluorescent dyes, such as acrinidine orange which are active only within nucleic acid containing cells. Labeled cells in the pellet 235 are excited by the impinging light and emit light 236 of a wavelength longer than a threshold wavelength. The light 236 impinges onto a detector 237. Embodiments of the detector 237 comprise a CCD camera, photodiode, photomultiplier, or human eye. The upper layer 232 may be dyed with filtering agents configured to selectively pass light 236 longer than a threshold wavelength emitted by the cells in the pellet 235 to improve accuracy of cell detection. The detector 237 may determine estimated cell concentration by scanning along the sedimentation column and can be based on total fluorescent signal. The embodiment of the sedimentation column 231 described here using dyes with filtering agents may be combined with lenses as described in FIGS. 19, 20 and 21 to enhance accuracy of cell count estimations. The features described with respect to the sedimentation column 231 may also be used to enhance detection in particle-based immunoassays. The features described with respect to the sedimentation column 231 may also be incorporated into the sedimentation column 211 of FIG. 21.

FIG. 24 shows an embodiment of a sedimentation column 241 enclosed by an upper layer 242 of polymer and a lower layer 243 of polymer. The upper layer 242 and the lower layer 243 may be joined by processes including ultrasonic welding or thermal bonding. A light source 244, such as an LED, sunlight, or room lighting, emits light that impinges a pellet 245 through the upper layer 242, wherein the polymer of the upper layer 242 is transparent. The pellet 245 scatters light 247 back towards the light source 244 due to the pellet's particulate nature while fluid 246 transmits light. If the lower layer 243 is doped or covered with light absorbing material, such as carbon black or other light absorbing pigments, part of the light transmitted by the fluid 246 will be absorbed, enhancing optical contrast between the pellet 245 and the fluid 246. The scattered light 247 may be detected by a detector, such as a CCD camera, mobile communication device, or human eye, to estimate cell concentration. In this embodiment, the light source 244 is perpendicular to the upper layer 242. The light source 244 may also be placed in parallel with or in the upper layer 242 and still scatter light 247 toward a viewer or detector. This configuration may further increase optical contrast of the pellet 245 by avoiding or minimizing interfering reflection off of planar surfaces of the layers 242 and 243.

FIG. 25 illustrates an example of a sedimentation column of a fluid following centrifugation, wherein the fluid comprises particles or materials with a density higher than the fluid's density but lower than density of certain cells or particulates in the fluid. The sedimentation column comprises metering marks 252 and numbers 253. Following centrifugation, the intermediate density particles or materials form an intermediate layer 254 between the pellet 255 of compacted cells and the fluid 256. The intermediate layer 254 may comprise distinctively colored particles or materials such as dyed polystyrene or another polymer in order to enhance optical contrast of an interface between the pellet 255, intermediate layer 254, and fluid 256. The user can estimate initial concentration of cells in the sample by reading a number 253 closest to a metering mark 252 closest to an interface between the pellet 255 and the intermediate layer 254.

FIG. 25 alternately may represent an example of the sedimentation column of a fluid following centrifugation, wherein the fluid was mixed with a dye prior to centrifugation that identifies dead cells. For example, the dye can selectively partition into dead cells but not living cells. It is known in the art that dead or immotile sperm cells have a density lower than the density of living and motile sperm cells. The sedimentation column comprises metering marks 252 and numbers 253. Following centrifugation, the fluid separates into layers with a fluid layer 256 closest to the center of the centrifugation, a live cells layer or a pellet 255 furthest from the center of the centrifugation, and a dead cells layer 254 with intermediate density in between the two layers 256 and 255. Living cells exclude the dye and therefore are visually distinct from the dead cells layer 254 and fluid layer 256 which also exhibit the color of the dye. The user can estimate initial concentration of living cells in the fluid by reading a number 253 closest to a metering mark 252 closest to an interface between the pellet 255 and the dead cells layer 254. The user can also estimate number of dead cells from the visually distinct dead cell layer 254. As described previously, an intermediate density layer formed from polymer fragments or particles may be mixed into the fluid prior to centrifugation to enhance the contrast between the dead cells layer 254 and pellet 255.

FIGS. 26 and 27 illustrate various embodiments of mechanisms for attaching a cartridge to a motor of an instrument. These embodiments may be used with any of the cartridges or instruments described herein, or may be used to attach the cartridge to other instruments outside of those described herein. In any embodiment, the cartridge, the motor shaft or an adaptor configured to attach to the motor may comprise a magnetic material, providing a mechanism for attaching the cartridge to the motor.

FIG. 26 shows an embodiment of a schematic for attaching a cartridge 261 to a motor 262 of an instrument. The cartridge comprises a cavity 263. The cavity 263 comprises a first diameter less than a second diameter of a shaft 264 of the motor 262. To attach the cartridge 261 to the motor 262, the shaft 264 is press-fit into the cavity 263. Material used in the first diameter of the cavity 263 and elastic modulus of material used for the cartridge 261 may be selected such that a tight friction fit is established between the shaft 264 and cavity 263 of the cartridge 261 allowing rotation of the cartridge 261 when attached to the instrument.

FIG. 27 shows a second embodiment of a schematic for attaching a cartridge 271 to a motor 275 of an instrument 272. The cartridge comprises a cavity 273. The cavity 273 comprises a shape and the adaptor 274 comprises the same shape and is configured to fit in the cavity 273. The adaptor 274 is attached to the motor 275. To attach the cartridge to the motor, the adaptor 274 is press-fit into the cavity 273. Material used in the first diameter of the cavity 273 and elastic modulus of material used for the cartridge 271 may be selected such that a tight friction fit is established between the motor 275 and cavity 273 of the cartridge 271 allowing rotation of the cartridge 271 when attached to the instrument. The material of the adaptor 274 may comprise notches configured to allow the adaptor to flex creating a secure fit between the cartridge and adaptor. In another embodiment, the motor 272 may comprise a cavity-containing socket and the cartridge 271 may comprise a corresponding projection. Additional projections may be added to the adaptor 274 of the motor 272 in order to create a "snap" fit with the cartridge.

FIGS. 28-33 show various embodiments of instruments. These embodiments may be used with any of the cartridges described throughout and any of the attachment mechanisms described throughout. In addition, the cartridges can be attached to other instruments outside of those described here.

FIG. 28 shows an embodiment of a schematic of an instrument configured to rotate a cartridge 287. This embodiment may be used with any of the cartridges described throughout. The instrument comprises an enclosure 281, a printed circuit board 282, a motor 283, a lid 284, a switch 285, indicator LEDs 286, or any combination thereof. In alternative embodiments, the printed circuit board 282 may be any suitable controller coupled to the motor 283, the switch 285, or the indicator LEDs 286. The printed circuit board 282 may comprise one or more microcontrollers, an oscillator crystal, motor control transistors, power regulating circuitry, LEDs, user switches, and other circuitry necessary to operate the instrument or provide feedback to users. The printed circuit board 282 may be configured to detect whether or not a cartridge is attached to the instrument. In one embodiment, the printed circuit board 282 detects whether or not the cartridge is attached by differences in voltage (such as by back EMF) generated by the motor when rotating with and without the attached cartridge. For example, the instrument comprises a plurality of reference points from which the printed circuit board 282 can measure voltage among the plurality of reference points. Such detection may be advantageous because an additional switch to activate the instrument will not be necessary, reducing the instrument cost and making the instrument easier to use. The printed circuit board 282 can be configured to provide variable power to the motor for specified intervals of time in order to mix and spin the cartridge as described above. Furthermore, the printed circuit board 282 can be configured to control illumination of indicator LEDs 286 to notify a user of significant events including completion of an assay. The lid may comprise a structure 288 which closes on the cartridge 287 during lid closure, the structure 288 configured to ensure secure attachment of the cartridge 287 to the motor 283 during operation. The instrument may be powered by an external AC-DC power converter 289 or other suitable power mechanism configured to plug into an electrical socket or may contain alternately or additionally a set of batteries configured to provide electrical power. If electrical power is provided by batteries, the printed circuit board 282 may be configured to adjust power provided to the motor to maintain consistent spin rates and compensate for variations in battery voltage. In addition, the printed circuit board 282 can be configured to terminate rotation and display warning signs such as flashing LEDs if battery voltage decreases below a threshold level. The lid or enclosure may also comprise a latch configured to prevent rotation of the cartridge when the lid is open, ensuring safety for the user. The lid or enclosure may also include a switch or other mechanism configured to trigger instrument operation. In some embodiments, the lid may include one or more magnets that trigger activation of the motor or other operations of the instrument when the one or more magnets are brought a threshold distance away from one or more sensors in the instrument. Such embodiments may be advantageous because an additional switch to activate the instrument is not required and instrument cost is reduced, making it easier and/or more intuitive to use.

Figure 29:
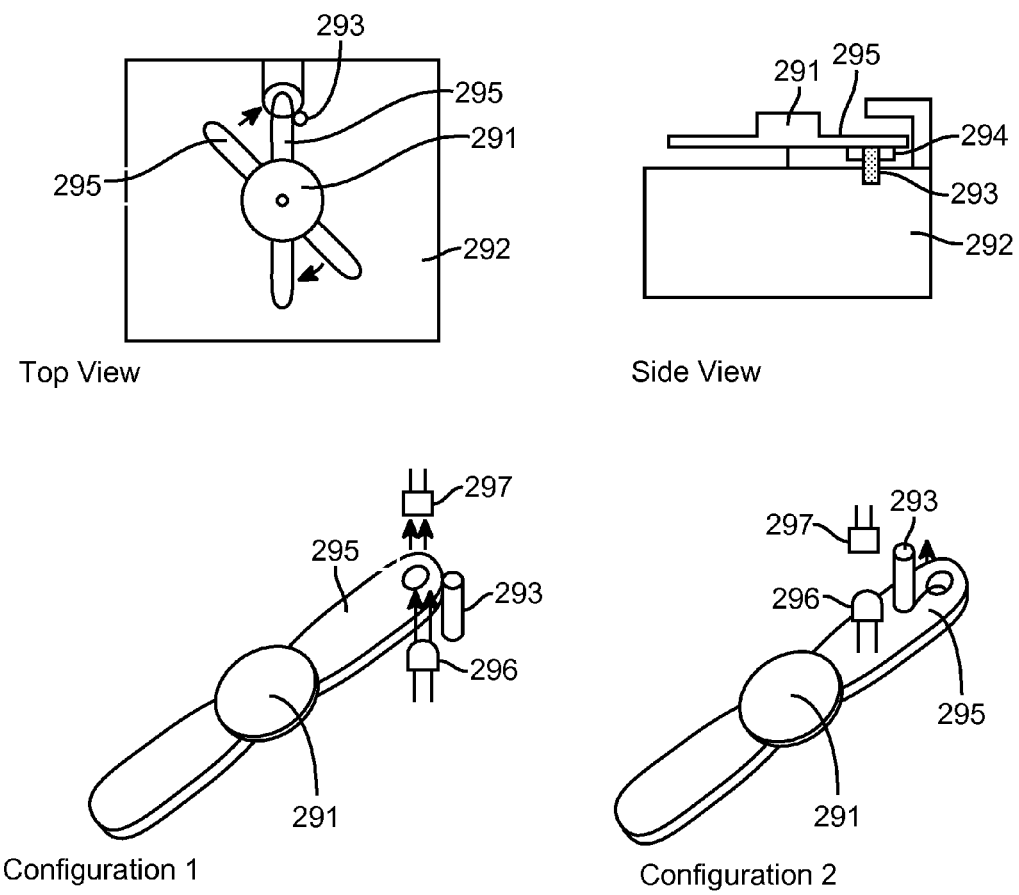
FIG. 29 illustrates a top view and a side view of a cartridge and an instrument and a configuration 1 state and configuration 2 state of the cartridge, in accordance with an embodiment of the invention.

FIG. 29 shows a top view, a side view, a configuration 1 view and a configuration 2 view of another embodiment of a configuration of a cartridge 291 and instrument 292 intended for use in fluorescent detection assays. The configuration can also be used for visual inspection methods. Any of the cartridges described throughout can be used with the configuration. The instrument comprises an impinging element 293 that comprises flexible material and intersects with a portion of the cartridge or a catch feature on the cartridge 294 configured to stop the cartridge at a specified location within the instrument. The flexible material of the impinging element 293 or material of the cartridge catch feature 294 may be selected such that, due to the flexible material, the cartridge is configured to rotate freely while the motor provides sufficient power. However, the cartridge is configured to stop at a specified location when power is reduced or withdrawn from the motor. Therefore, a portion 295 of the cartridge to be analyzed can be aligned with a light source 296 and/or photodetector 297 for static analysis without additional control inputs from the instrument. The photodetector and light source may be positioned on opposite sides of the cartridge as shown in configuration 1 of FIG. 29 or at an angle from each other on the same side, such as top or bottom, of the cartridge as shown in configuration 2 of FIG. 29.

Figure 30:
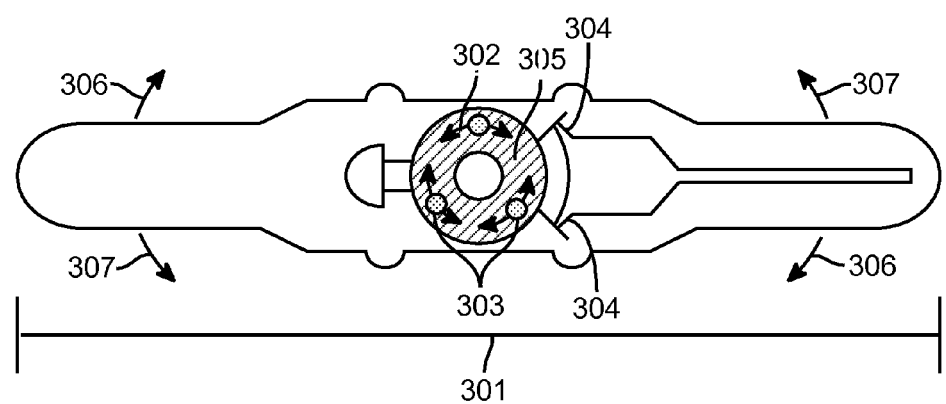
FIG. 30 illustrates an embodiment of a cartridge containing dense objects, in accordance with an embodiment of the invention.

FIG. 30 demonstrates mechanical agitation of fluid, such as semen, or other viscous or particulate containing samples. A cartridge 301 contains a central cavity 302 which receives the fluid 305. This may be used with any of the cartridges described throughout. The central cavity may contain dense objects 303 which comprise a diameter larger than diameter or width of fluidic channels 304, the fluidic channels 304 directed radially outward from the central cavity. The cartridge may be accelerated first in a first direction 306, then in a second direction 307 and then continuing this alternating motion for a defined interval of time. Alternately, the cartridge may be accelerated in the first direction 306 and allowed to come to a stop, with this pattern of accelerating in one direction and stopping repeated for a defined interval of time. These motion patterns causes agitation of the fluid and may cause any enclosed dense objects 303 to move relative to the fluid, aiding in mechanical agitation and configured to break down fluid viscosity or break up clumps of particles in the fluid.

Figure 31:
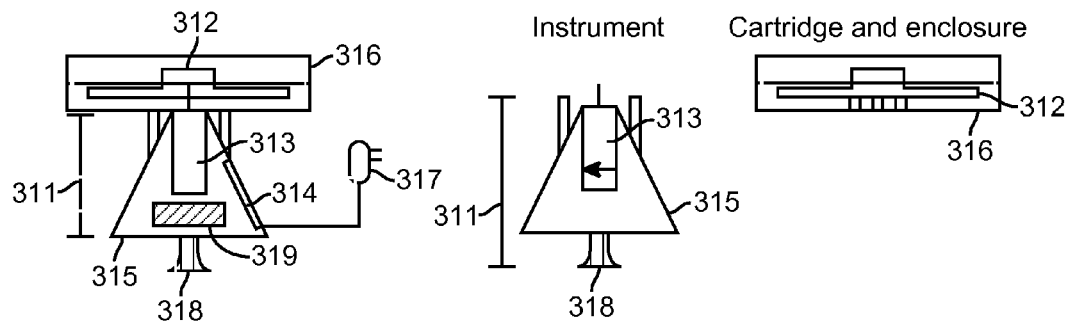
FIG. 31 illustrates a cartridge, an enclosure for the cartridge, and an instrument with a tapered form factor, in accordance with an embodiment of the invention.

FIG. 31 illustrates a side view of an instrument 311 and cartridge 312, the instrument 311 and the cartridge 312, the cartridge and instrument for fluid, semen or particulate analysis. The instrument may be used with any of the cartridges described throughout. The instrument comprises a motor 313, a printed circuit board 314, a motor enclosure 315, a cartridge enclosure 316, and power supply 317 such as a battery. In one embodiment, the motor enclosure 315 is tapered. In one embodiment, the cartridge enclosure 316 is form-fitting to the cartridge and openable. A user switch and indicator LEDs may also be included (not shown). The cartridge and cartridge enclosure are configured to be fully detachable from the instrument and may both be disposable. Once closed, the cartridge enclosure can be configured to be irreversibly bond together a first side and a second side of the cartridge, preventing the user from opening the cartridge during operation or following processing of the fluid. To prevent excessive noise, vibration, and movement of the instrument during operation, such as centrifugation, the instrument may comprise a securing mechanism 318, such as a suction cup or rubber feet, attached to the bottom surface of the instrument. The instrument may comprise weighted ballast 319 in the form of dense material, such as metal plates, configured to prevent the instrument from tipping over during operation.

Figure 32:
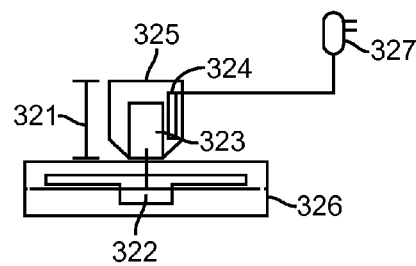
FIG. 32 illustrates an alternative configuration of a cartridge and an instrument, in accordance with an embodiment of the invention.

FIG. 32 illustrates another embodiment of an instrument 321 and a cartridge 322 for fluid, semen or particulate analysis in which the instrument is plugged into the cartridge and cartridge enclosure 326 from above. This may be used with any of the cartridges described throughout. The instrument comprises a motor 323, control board 324, motor enclosure 325, cartridge enclosure 326, and power supply 327 such as a battery. In one embodiment, the motor enclosure 325 is tapered. In one embodiment, the cartridge enclosure 316 is form-fitting to the cartridge. A user switch and indicator LEDs may also be included (not shown). The instrument may comprise weighted ballast in the form of dense material, such as metal plates, configured to prevent the instrument from tipping over during operation.

Figure 33:
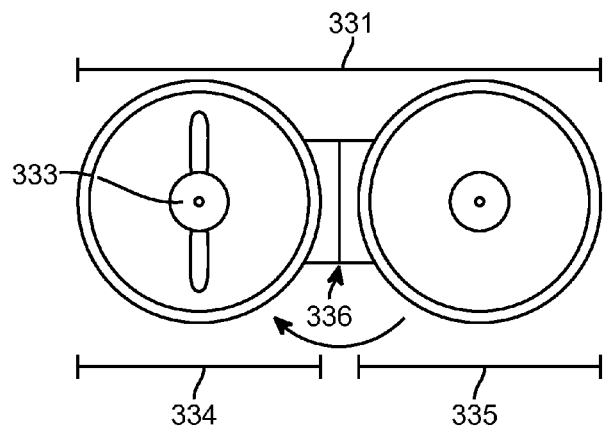
FIG. 33 illustrates an open enclosure of a cartridge, in accordance with an embodiment of the invention.

FIG. 33 diagrams an embodiment of a configuration of a cartridge enclosure 331 which is detachable from the instrument 311 (of FIG. 31) and comprises a cartridge 333. This may be used with any of the cartridges described throughout. The enclosure 331 may comprised a bottom half 334, top half 335, and a living hinge 336. The enclosure 331 can be opened, as shown in FIG. 33, configured to allow a user to add fluid to the cartridge 333. Following fluid addition, the user may close the cartridge enclosure 331. The combined cartridge 333 and closure 331 may be connected to the instrument 311 to rotate the cartridge 333 during centrifugation. In one embodiment, the cartridge and enclosure may be made from polymer and be disposable.

FIGS. 34-37 illustrate embodiments in which additional liquid reagents are added to a cartridge to separate different types of particles from cells, such as sperm cells. Any of these embodiments may be used with any of the cartridges or instruments described throughout.

Figure 34:
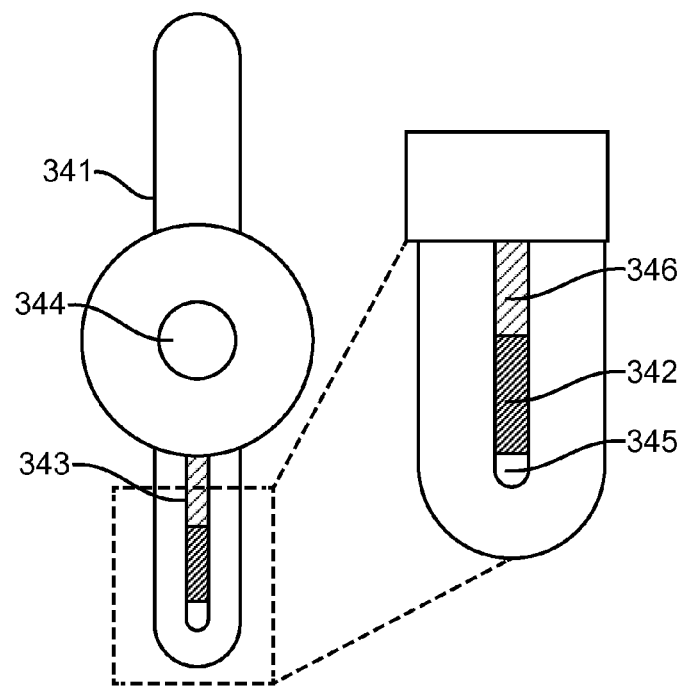
FIG. 34 illustrates a sedimentation column with a density medium, in accordance with an embodiment of the invention.

FIG. 34 illustrates an embodiment in which a liquid medium of defined density is used to separate particulates based on unique physical characteristics of the particulates. In one embodiment, the cartridge 341 is loaded with a volume of a density medium 342; the density medium 342 comprises a fluid medium of a defined density. The density medium 342 occupies a defined volume of a sedimentation column 343 integrated into the cartridge 341. The sedimentation column, the sample directing cavity, and the sample entry cavity of all cartridges described herein are configured to be able to hold the density medium. The density medium may be stored within a cartridge or included as part of a kit. The sample fluid is loaded through a central cavity 344 of the cartridge and the cartridge is spun at a specified rotation rate for an interval of time such that a defined volume of the sample fluid layers upon the density medium 342 in the sedimentation column 343. During centrifugation, particulates in the sample fluid that comprise a higher density than density of the density medium 342 will sediment to the end of the sedimentation column during centrifugation, forming a pellet 345. The height of the pellet 345 may be measured to estimate initial concentration of higher density particulates as described previously. Excess fluid and particulates comprising a density less than density of the density medium will remain suspended as a supernatant 346. The sample fluid may comprise semen, and the particulates may comprise sperm cells. The unique physical characteristics of the sperm cells may comprise a density, the density characteristic of cell motility, viability, or morphology. In some embodiments, the density medium may comprise a fluid of specified density configured to separate sperm cells from other particulates found in semen such as cell fragments and leukocytes (i.e. the density medium is less dense than the sperm cells and denser than the other particulates). In this embodiment, the pellet 345 may be measured to estimate the concentration of sperm cells without interference from other particulates in semen. In some embodiments, the density medium 342 may comprise a fluid of specified density configured to separate motile from non-motile sperm cells (i.e. the density medium is more dense than non-motile sperm cells and less dense than motile sperm cells). In this embodiment, the pellet 345 may be measured to estimate the concentration of motile sperm cells. In another embodiment, the density medium 342 may comprise a specified density configured to isolate X-chromosome containing sperm cells from Y-chromosome containing sperm cells (X-chromosome containing sperm cells are on average denser than Y-chromosome containing sperm cells).

Figure 35:
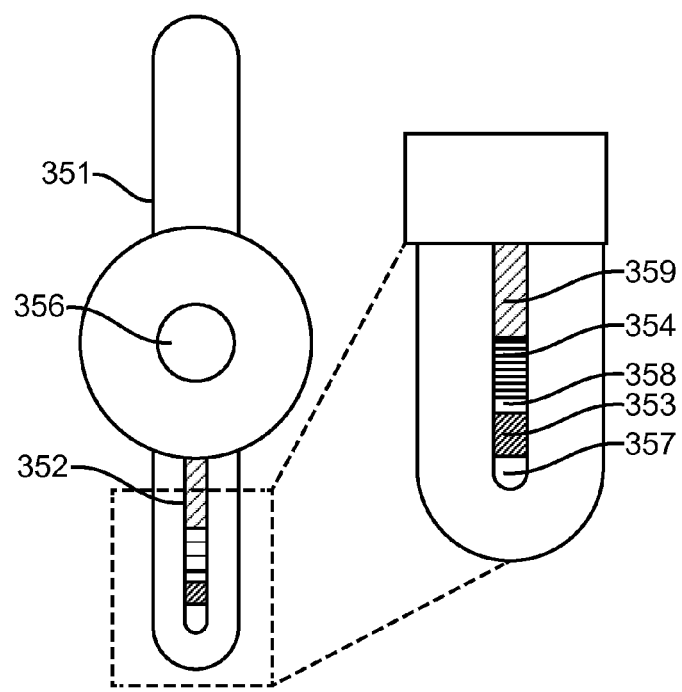
FIG. 35 illustrates a sedimentation column with two density media, in accordance with an embodiment of the invention.

FIG. 35 diagrams an embodiment of a cartridge 351 in which two or more liquid density media comprising defined densities are loaded into a sedimentation column 352, forming a continuous or discontinuous density gradient. Particulates in the sample may be separated based on unique physical characteristics of the particulates and separate into the density gradient. In one embodiment, the density media comprise a first density medium 353, first loaded into the sedimentation column 352, and a second density medium 354, loaded into the sedimentation column 352 following the first density medium 353. The sample fluid is loaded through a central cavity 356 of the cartridge 351 and the cartridge is spun at a specified rotation rate for an interval of time such that a defined volume of the sample fluid layers upon the density media 353 and 354 in the sedimentation column. During centrifugation, particulates comprising a density higher than density of the first density medium 353 and density of the second density medium 354 will form a pellet 357 at the bottom of the sedimentation column. Particulates comprising a density lower than density of the first density medium 353 but higher than density of the second density medium 354 will concentrate at an interface 358 of the two density media 353 and 354. Excess sample fluid and particulates comprising a density less than the density media 353 and 354 will remain suspended as supernatant 359.

Figure 36:
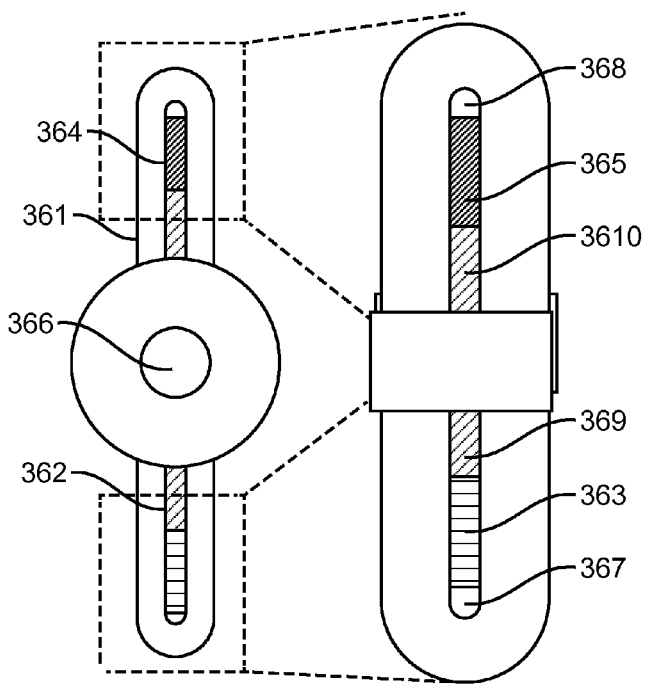
FIG. 36 illustrates two sedimentation columns with a density medium in each, in accordance with an embodiment of the invention.

FIG. 36 illustrates an embodiment of a cartridge 361 in which two or more liquid density media comprising defined densities are loaded into two sedimentation columns 362 and 364 on the cartridge. A first sedimentation column 362 is filled with a first density medium 363, while a second sedimentation column 364 is filled with a second density medium 365. For example, the clinical fluid is loaded through a central cavity 366 and the cartridge is centrifuged at a specified rotation rate for an interval of time such that a defined volume of the sample layers upon each pre-loaded density media 363 and 365 in the individual sedimentation columns 362 and 364, respectively. During centrifugation, particulates in the clinical fluid are isolated based on density in each sedimentation column, forming pellets 367 and 368 at the end of each sedimentation column 362 and 364 respectively. Excess clinical fluid and particulates comprising a density less than density of either density media will remain suspended as supernatants 369 and 3610. This embodiment may be extended to a plurality of sedimentation columns and density media. For example, certain embodiments may comprise a cartridge with three or more sedimentation columns, each containing zero, one, or more density media.

Figure 37:
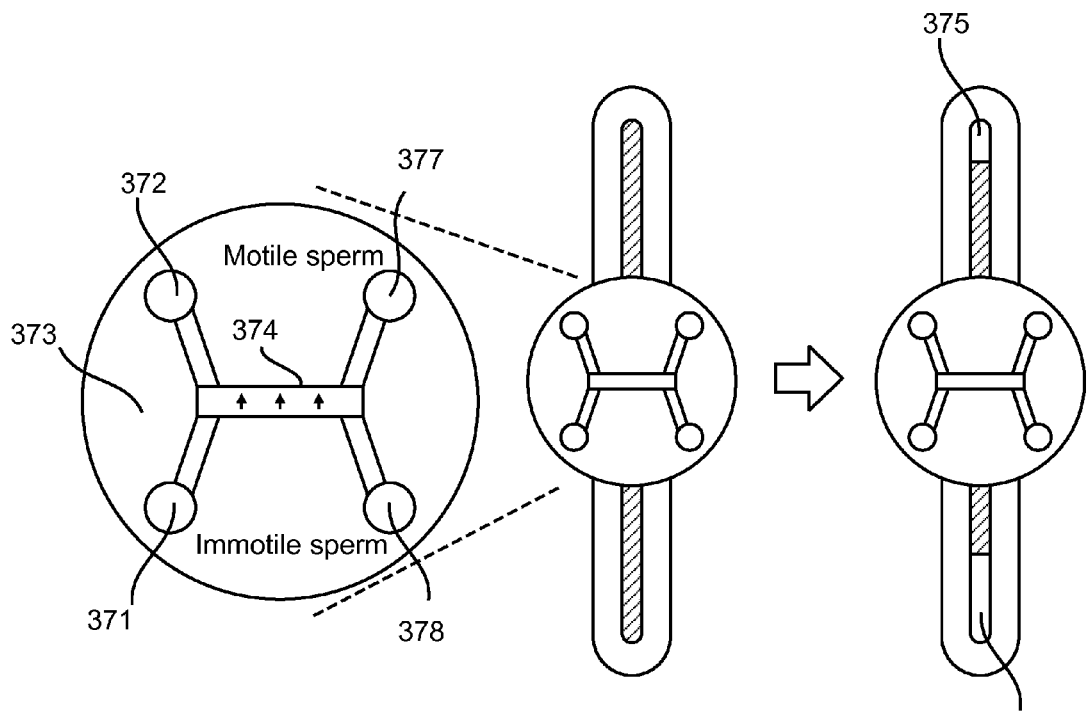
FIG. 37 illustrates a cartridge configured to discern motility of cells, in accordance with an embodiment of the invention.

FIG. 37 illustrates an embodiment of a cartridge in which diffusion is used to isolate motile from immotile cells, such as sperm cells, prior to centrifugation, thereby enabling quantification of total cells and percent of cell motility. The fluid is loaded to the sample inlet channel 371 and a sheath fluid is loaded into the corresponding inlet channel 372 on the other side of the central section 373 of the cartridge. The fluid and sheath fluid flow via gravity-driven flow or other pressure source from one side to the other side of the central section 373. Within the joint central channel 374, motile cells are able to swim from the sample inlet fluid stream including inlets 371 and 372 to the sheath fluid stream including outlets 377 and 388, thereby separating from immotile cells which remain in the lower channel. Following separation, the cartridge is rotated at a specified rotation rate for an interval of time such that motile cells in the upper channel are transported to the upper sedimentation channel, while cells in the lower channel are transported to the lower sedimentation channel. Following rotation, volumes of pellets 375 and 376 in the upper and lower sedimentation channels, respectively, are used to quantify total cell count and percent motility.

The above description and figures provide embodiments of different designs that can be incorporated in the devices, systems, and methods described herein. More, fewer, and/or different components and steps than those described herein may be used with the devices, systems, and methods. Different cartridges described throughout can be used in any of the different kits described throughout, and components of the kits described throughout can vary.

What is claimed is:

1. An apparatus comprising: a cartridge having a first end, a second end, an underside, and a connecting mate on the underside, the cartridge having a length that is longer than a width of the cartridge, the cartridge configured to be rotated about a rotational axis of the cartridge to cause sedimentation of particulates or cells in a received sample, wherein the rotational axis is aligned with the connecting mate of the cartridge, and the rotational axis is located between the first end and the second end of the cartridge, the connecting mate configured to connect the cartridge to a connecting mechanism of an instrument for rotation of the cartridge, the cartridge comprising:
   a central cavity configured to hold the received sample;
   a sedimentation column configured to be in fluid communication with the central cavity, the sedimentation column comprising:
     a channel or a second cavity with a cross-sectional area that is less than a cross-sectional area of the central cavity; and
   a sample directing cavity comprising a first opening connected to the central cavity and a second opening connected to the sedimentation column, the first opening comprising a first cross-sectional area and the second opening comprising a second cross-sectional area that is less than the first cross-sectional area, the sample directing cavity configured to hold a defined volume of the received sample and configured to direct cells into the sedimentation column during rotation of the cartridge.

2. The apparatus of claim 1, further comprising an instrument configured to receive and rotate the cartridge during an operating mode, the instrument comprising:

a motor;
a connecting mechanism configured to mate the instrument with the cartridge at least during the operating mode; and
a controller configured to control amount of power provided to the motor.

3. The apparatus of claim 2, wherein the controller is further configured to control any from a group consisting of: spin rate of the motor, direction or spin of the motor, duration of spin of the motor, and any combination thereof.

4. The apparatus of claim 2, further comprising a plurality of emitters coupled to the controller.

5. The apparatus of claim 4, wherein the controller is further configured to control amount of light emitted by the emitters.

6. The apparatus of claim 2, wherein the controller is further configured to detect a state of the instrument, the state selected from a group consisting of: whether or not a lid of the instrument is opened or closed, voltage of a battery in the instrument, whether or not the cartridge is attached to the instrument, and rate of rotation of the cartridge.

7. The apparatus of claim 2 wherein the instrument further comprises a plurality of reference points, each reference point comprising a voltage value, and wherein the controller is further configured to:
measure a difference in voltage value at the plurality of reference points in the instrument at a plurality of specified moments of time when the motor is spinning; and
control the spin rate, or duration of spin of the motor by providing power, wherein the power provided is based on the difference in voltage at the plurality of reference points.

8. The apparatus of claim 2, wherein the instrument further comprises a plurality of reference points, each reference point comprising a voltage value, and wherein the controller is further configured to detect whether or not the cartridge is attached to the motor by providing power to the motor and measuring the voltage value at the plurality of reference points.

9. The apparatus of claim 2, wherein the motor further comprises a motor terminal, the instrument comprises one or more reference voltages, and the controller is further configured to detect whether or not the cartridge is attached to the motor by providing power to the motor for a first interval of time, stopping providing power to the motor for a second interval of time, and measuring a voltage difference across the motor terminal and the one of the one or more reference voltage or the voltage difference across a battery of the instrument.

10. The apparatus of claim 2, wherein the instrument further comprises a magnet and a sensor configured to detect magnetic fields.

11. The apparatus of claim 10, wherein the instrument further comprises a lid, the magnet is incorporated into the lid of the instrument, and the sensor is incorporated into the instrument such that, when the instrument lid is closed, a first distance between the magnet and the sensor allows the sensor to detect magnetic fields from the magnet.

12. The apparatus of claim 11, wherein the sensor is coupled to the controller and the controller is further configured to detect a change in magnetic field through the sensor, the change in magnetic field corresponding to whether or not the first distance between the magnet and sensor is less than a threshold distance indicative of a closed lid.

13. The apparatus of claim 12, wherein the controller is further configured to stop powering the motor if the distance between the magnet and the sensor is greater than the threshold distance.

14. The apparatus of claim 1, wherein the connecting mate of the cartridge is configured to attach to an in-built shaft of the connecting mechanism.

15. The apparatus of claim 1, wherein the sample directing cavity is configured to receive a specified volume of the received sample from the central cavity upon rotation of the cartridge at a first rate.

16. The apparatus of claim 15, wherein the sample directing cavity is integrated in the cartridge at a slope configured to direct cells into the sedimentation column when the cartridge is rotated at a second rate, the second rate faster than the first rate.

17. The apparatus of claim 16, wherein the cartridge further comprises shallow channels connecting the first opening of the sample directing cavity to the central cavity such that the received sample can move from the central cavity to the sample directing cavity only through the shallow channels, the shallow channels comprising a third cross-sectional area configured to prevent the received sample from moving from the central cavity to the sample directing cavity when the cartridge is not being rotated.

18. The apparatus of claim 17, wherein the cartridge further comprises additional channels connected to the central cavity or shallow connecting channels, configured to receive particulates or cells from the received sample in the cavity that were not directed to the sample directing cavity upon rotation at the first rate.

19. The apparatus of claim 17, wherein the cartridge further comprises an overflow chamber connected to the central cavity by channels comprising a fourth cross-sectional area substantially smaller than a fifth cross-sectional area of the central cavity, the channels configured to prevent the received sample from moving from the central cavity to the overflow chamber during the first rate of rotation and to allow the received sample to move from the cavity to the overflow chamber during the second rate of rotation.

20. The apparatus of claim 16, wherein the cartridge further comprises an overflow chamber connected to the central cavity, and wherein the overflow chamber is configured such that the overflow chamber and the sample directing cavity equally distribute mass around the center of the cavity and balance the cartridge upon rotation.

21. The apparatus of claim 16, wherein the central cavity is configured such that particulates or cells from the received sample not inside the sample directing cavity and the sedimentation column after rotation at the first rate form a pellet outside of the sedimentation column upon rotation at the second rate.

22. The apparatus of claim 16, wherein the sedimentation column is further configured to sediment a pellet of cells comprising visible borders to an unaided human eye during the second rotation rate.

23. The apparatus of claim 1, further comprising a cylindrical lens incorporated into a polymer structure above the sedimentation column configured to optically magnify a width of a pellet of the sedimented cells and to aid in visualization of the pellet.

24. The apparatus of claim 1, further comprising a cell label included in an enclosure integrated in the cartridge.

25. The apparatus of claim 24, wherein the cell label is acrinidine orange.

26. The apparatus of claim 1, further comprising a fluid label or water soluble label included in an enclosure integrated in the cartridge.

27. The apparatus of claim 26, wherein the fluid label or water soluble label is configured to enhance contrast between the cells and the sample.

28. The apparatus of claim 26, wherein the fluid label or water soluble label is configured to enhance contrast between living and dead cells.

29. The apparatus of claim 28, wherein the fluid label is trypan blue.

30. The apparatus of claim 1, wherein the cartridge further comprises formed polymer layers containing selective light absorbing pigments.

31. The apparatus of claim 30, wherein the pigments within a polymer layer of the cartridge are configured to selectively absorb illumination wavelengths allowing visual fluorescent identification of a height of a pellet of the sedimented cells.

32. The apparatus of claim 1, wherein the cartridge is coated with selective light reflecting dichroic layers.

33. The apparatus of claim 1, further comprising an instrument configured to receive the cartridge and to provide illumination of the sedimentation column from below to cause fluorescent emission by a cell label of the cells.

34. The apparatus of claim 1, wherein a lower element of the cartridge is pigmented and an upper element of the cartridge is transparent such that illumination of the sedimentation column from above causes light to be scattered off of the cells in the sedimentation column and absorbed by the pigmented lower element of the cartridge in locations along the sedimentation column corresponding to an absence of cells, aiding in visualizing a pellet of the sedimented cells.

35. The apparatus of claim 1, wherein a lower element of the cartridge is opaque and an upper element and side elements of the cartridge are transparent such that illumination of the sedimentation column from a side of the cartridge causes light to scatter off of the cells in the sedimentation column and enhances contrast.

36. The apparatus of claim 1, wherein the received sample is semen and the cells are sperm cells.

37. The apparatus of claim 1, further comprising one or more density media in the sedimentation column, in the central cavity, or in the sample directing cavity.

38. The apparatus of claim 37, wherein the cartridge further comprises an evaporation barrier and the cavity, the sedimentation column, and the sample directing cavity are configured to hold the density media.

39. The apparatus of claim 37, wherein the one or more density media comprise a density higher than density of seminal plasma and lower than density of sperm cells, the one or more density media configured to separate sedimented sperm cells from seminal fluid and other particulates in the received sample within the sedimentation column.

40. The apparatus of claim 37, wherein the one or more density media comprise a density higher than density of immotile sperm cells and lower than density of motile sperm cells the one or more density media configured separate motile cells from seminal fluid, immotile cells, and other particulates within the sedimentation column.

41. The apparatus of claim 37, wherein the one or more density media comprise a density higher than density of dead cells and lower than density of live cells, the one or more density media configured separate live cells from seminal fluid, dead cells, and other particulates within the sedimentation column.

42. The apparatus of claim 1, wherein the apparatus further comprises one or more additional sedimentation columns and one or more respective sample directing cavities.

43. The apparatus of claim 42, wherein the apparatus further comprises one or more density media in the one or more sedimentation columns, in the central cavity, or in the one or more sample directing cavities.

44. The apparatus of claim 1, wherein the apparatus further comprises one or more colored or fluorescent polymer floats in the sedimentation column, in the central cavity, or in the sample directing cavity.

45. The apparatus of claim 44, wherein the received sample comprises a first cell type with a first density and a second cell type with a second density, wherein the first density is higher than the second density and one of the one or more floats comprise a density less than the first density and higher than the second density.

46. The apparatus of claim 44, wherein the float comprises a first density higher than a second density of seminal plasma and lower than a third density of sperm cells, the float configured to mark a boundary between sedimented sperm cells and seminal plasma within the sedimentation column.

47. The apparatus of claim 44, wherein the float is selected from a group consisting of: fluorescent polystyrene beads, colored polystyrene beads, and chips of polystyrene.

48. The apparatus of claim 1, wherein the sedimentation column further comprises at least one marking configured for allowing an estimate of cell concentration to be visually ascertained from a volume of the sedimented cells within the sedimentation column.

49. The apparatus of claim 1, wherein the sedimentation column further comprises a plurality of portions, each portion comprising a cross-sectional area different than another cross-sectional area of another portion in the plurality of portions.

50. The apparatus of claim 49, wherein the sedimentation column further comprises a plurality of markings configured to aid a user in estimating cell concentration of the sedimented cells within the sedimentation column and the plurality of portions of the sedimentation column comprises varying cross-sectional areas configured to further aid a user in measuring cell concentration of the sedimented cells.

51. The apparatus of claim 1, wherein the cartridge comprises dense solid objects configured to assist in agitation of the received sample upon rotation.

52. The apparatus of claim 1, wherein at least a portion of the sedimentation column comprises material that is transparent.

53. The apparatus of claim 1, wherein the length of the cartridge is more than twice the width of the cartridge.

54. The apparatus of claim 1, wherein the central cavity further comprises a diameter, wherein the diameter is not more than half the length of the cartridge.

55. The apparatus of claim 1, wherein the sample directing cavity extends radially outward from the cavity and radially inward from the sedimentation column.

56. A kit comprising:
   the cartridge of claim 1;
   an instrument comprising a connecting mechanism to securely mate the instrument with the cartridge, the instrument configured to rotate the cartridge;
   a transfer device; and
   a sample collection cup.

57. The kit of claim 56, wherein the transfer device further comprises one or more metering lines.

58. The kit of claim 56, wherein the sample collection cup further comprises a material configured to reduce viscosity of a received sample.

59. The kit of claim 58, wherein the received sample is semen and the material is an enzyme configured to break down proteins in semen.

60. The kit of claim 58, wherein the kit further comprises an imaging device configured to assist in quantifying sedimented cell pellets in a sedimentation column of the cartridge.

61. The kit of claim 56, wherein the kit further comprises a density medium.

62. The apparatus of claim 1, wherein the rotational axis of the cartridge is centered at a rotation center of the central cavity.

63. The apparatus of claim 1, wherein the central cavity, the sedimentation column, and the sample directing cavity are aligned along a radial axis directed radially outward from the central cavity.

64. The apparatus of claim 1, wherein a surface of the central cavity, a surface of the sedimentation column, and a surface of the sample directing cavity are coplanar.

65. The apparatus of claim 1, wherein a cross-sectional area of the sample directing cavity and the sedimentation column together form a funnel shape.

\* \* \* \* \*